United States Patent
Ogilvie et al.

(10) Patent No.: US 6,616,669 B2
(45) Date of Patent: *Sep. 9, 2003

(54) METHOD FOR THE CORRECTION OF SPINAL DEFORMITIES THROUGH VERTEBRAL BODY TETHERING WITHOUT FUSION

(75) Inventors: James Ogilvie, Edina, MN (US); Michael C. Sherman, Memphis, TN (US); Troy Drewry, Memphis, TN (US); Jean Saurat, Avrill (FR)

(73) Assignee: SDGI Holdings, Inc., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/905,018

(22) Filed: Jul. 13, 2001

(65) Prior Publication Data

US 2002/0007184 A1 Jan. 17, 2002

Related U.S. Application Data

(63) Continuation of application No. 09/421,207, filed on Oct. 20, 1999, now Pat. No. 6,299,613.
(60) Provisional application No. 60/130,909, filed on Apr. 23, 1999, now abandoned.

(51) Int. Cl.[7] .............................................. A61B 17/56
(52) U.S. Cl. ........................................................ 606/61
(58) Field of Search ................................ 606/61, 72, 90, 606/105; 128/898

(56) References Cited

U.S. PATENT DOCUMENTS

| 3,693,616 A | 9/1972 | Roaf et al. |
|---|---|---|
| 4,041,939 A | 8/1977 | Hall |
| 4,047,524 A | 9/1977 | Hall |
| 4,078,559 A | 3/1978 | Nissinen |
| 4,170,990 A | 10/1979 | Baumgart et al. |
| 4,263,903 A | 4/1981 | Griggs |
| 4,278,091 A | 7/1981 | Borzone |
| 4,321,002 A | 3/1982 | Froehlich |
| 4,369,769 A * | 1/1983 | Edwards ..................... 606/61 |
| 4,434,796 A | 3/1984 | Karapetian et al. |
| 4,454,875 A | 6/1984 | Pratt et al. |
| 4,485,816 A | 12/1984 | Krumme |
| 4,570,618 A | 2/1986 | Wu |
| 4,570,623 A | 2/1986 | Ellison et al. |
| 4,573,454 A | 3/1986 | Hoffman |
| 4,686,970 A | 8/1987 | Dove et al. |
| 4,723,540 A | 2/1988 | Gilmer, Jr. |
| 4,743,260 A | 5/1988 | Burton |

(List continued on next page.)

FOREIGN PATENT DOCUMENTS

| EP | 0 026 970 A1 | 4/1981 |
|---|---|---|
| EP | 0 127 994 | 12/1984 |
| EP | 0 478 470 A1 | 1/1992 |

(List continued on next page.)

OTHER PUBLICATIONS

U.S. patent application Ser. No. 09/421,976, Drewry et al., filed Oct. 1999.

(List continued on next page.)

Primary Examiner—Eduardo C. Robert
(74) Attorney, Agent, or Firm—Woodard, Emhardt, Moriarty, McNett & Henry LLP

(57) ABSTRACT

A fusionless method of treating spinal deformities in the spine of a child or young adult involves attaching a tether to vertebral bodies on the convex side of the spine. Deformities are treated by using the tether to selectively constrain growth in a portion of the convex side of the spine. One device for tethering the spine is a combination of a strand threaded through channels defined in a set of blocks attached to the vertebral bodies on the convex side of the spine. Another device useful in the method is to attach spinal staples, preferably made of a shape memory alloy, to vertebral bodies, the staples spanning the intervertebral disc space.

35 Claims, 19 Drawing Sheets

U.S. PATENT DOCUMENTS

| | | |
|---|---|---|
| 4,756,711 A | 7/1988 | Mai et al. |
| 4,776,851 A | 10/1988 | Bruchman et al. |
| 4,815,453 A * | 3/1989 | Cotrel .................. 606/61 |
| 4,870,957 A | 10/1989 | Goble et al. |
| 4,955,910 A | 9/1990 | Bolesky |
| 4,966,600 A | 10/1990 | Songer et al. |
| 4,998,936 A * | 3/1991 | Mehdian |
| 5,002,563 A | 3/1991 | Pyka et al. |
| 5,002,574 A | 3/1991 | May et al. |
| 5,011,484 A | 4/1991 | Breard |
| 5,030,220 A * | 7/1991 | Howland |
| 5,046,513 A | 9/1991 | Gatturna et al. |
| 5,053,038 A | 10/1991 | Sheehan |
| 5,089,009 A | 2/1992 | Green |
| 5,092,866 A | 3/1992 | Breard et al. |
| 5,092,868 A | 3/1992 | Mehdian |
| 5,108,395 A | 4/1992 | Laurain |
| 5,116,340 A | 5/1992 | Songer et al. |
| 5,180,393 A | 1/1993 | Commarmond |
| 5,190,546 A | 3/1993 | Jervis |
| 5,199,146 A | 4/1993 | Grover et al. |
| 5,209,756 A | 5/1993 | Seedhom et al. |
| 5,222,975 A | 6/1993 | Crainich |
| 5,246,443 A | 9/1993 | Mai |
| 5,261,908 A * | 11/1993 | Campbell, Jr. ........ 403/106 |
| 5,304,204 A | 4/1994 | Bregen |
| 5,306,301 A | 4/1994 | Graf et al. |
| 5,318,566 A | 6/1994 | Miller |
| 5,324,307 A | 6/1994 | Jarrett et al. |
| 5,342,396 A | 8/1994 | Cook |
| 5,352,229 A | 10/1994 | Goble et al. |
| 5,366,479 A | 11/1994 | McGarry et al. |
| 5,387,213 A | 2/1995 | Breard et al. |
| 5,395,372 A | 3/1995 | Holt et al. |
| 5,395,374 A | 3/1995 | Miller et al. |
| 5,415,658 A | 5/1995 | Kilpela et al. |
| 5,415,661 A | 5/1995 | Holmes |
| 5,417,690 A | 5/1995 | Sennett et al. |
| 5,423,820 A | 6/1995 | Miller et al. |
| 5,425,767 A | 6/1995 | Steininger et al. |
| 5,449,359 A | 9/1995 | Groiso |
| 5,454,814 A | 10/1995 | Comte |
| 5,456,722 A | 10/1995 | McLeod et al. |
| 5,474,557 A | 12/1995 | Mai |
| 5,476,465 A | 12/1995 | Preissman |
| 5,496,318 A | 3/1996 | Howland et al. |
| 5,536,270 A | 7/1996 | Songer et al. |
| 5,540,698 A | 7/1996 | Preissman |
| 5,540,703 A | 7/1996 | Barker, Jr. et al. |
| 5,545,168 A | 8/1996 | Burke |
| 5,551,871 A | 9/1996 | Besselink et al. |
| 5,569,253 A | 10/1996 | Farris et al. |
| D378,409 S | 3/1997 | Michelson |
| 5,607,425 A | 3/1997 | Rogozinski |
| 5,609,634 A | 3/1997 | Voydeville |
| 5,645,599 A | 7/1997 | Samani |
| 5,649,927 A | 7/1997 | Kilpela et al. |
| 5,653,711 A | 8/1997 | Hayano et al. |
| 5,660,188 A | 8/1997 | Groiso |
| 5,669,917 A | 9/1997 | Sauer et al. |
| 5,693,046 A | 12/1997 | Songer et al. |
| 5,702,395 A | 12/1997 | Hopf |
| 5,702,399 A | 12/1997 | Kilpela et al. |
| 5,707,395 A | 1/1998 | Li |
| 5,720,747 A | 2/1998 | Burke |
| 5,725,582 A | 3/1998 | Bevan et al. |
| 5,728,127 A | 3/1998 | Asher et al. |
| 5,741,260 A | 4/1998 | Songer et al. |
| 5,779,707 A | 7/1998 | Bertholet et al. |
| 5,785,713 A | 7/1998 | Jobe |
| 5,800,434 A * | 9/1998 | Campbell, Jr. ........ 606/60 |
| 5,853,414 A | 12/1998 | Groiso |
| 5,908,421 A | 6/1999 | Beger |
| 5,941,890 A | 8/1999 | Voegele et al. |
| 6,083,242 A | 7/2000 | Cook |
| 6,296,643 B1 | 10/2001 | Hopf et al. |
| 6,299,613 B1 | 10/2001 | Ogilive et al. |
| 6,325,805 B1 | 12/2001 | Ogilive et al. |

FOREIGN PATENT DOCUMENTS

| | | |
|---|---|---|
| EP | 0 545 830 A1 | 6/1993 |
| EP | 0 625 336 A2 | 11/1994 |
| FR | 2 603 794 | 3/1988 |
| FR | 2 628 312 | 9/1989 |
| FR | 2 694 696 | 2/1994 |
| FR | 2 743 490 A1 | 7/1997 |
| FR | 2 754 702 | 4/1998 |
| JP | 63-95060 | 4/1988 |
| RU | 1152582 | 4/1985 |
| WO | WO 91/16018 | 10/1991 |
| WO | WO 92/17122 | 10/1992 |
| WO | WO 94/01057 | 1/1994 |
| WO | WO 94/26192 | 11/1994 |

OTHER PUBLICATIONS

*The Use of Nickel–Titanium Alloy in Orthopedic Surgery in China*, Kuo, M.D.; Yang, M.D.; Zhang, M.D.; Yang; Yu, M.D.; Hong; Ke, M.D.; Cai, M.D.; Tao, M.D.; *Orthopedics*, Jan. 1989, vol. 12/No. 1.

"The Use of Ni–Ti as an Implant Material in Orthopedics", by Dr. J. Haasters, Prof. G. v. Salis–Solio, & Dr. G. Bensmann, pp. 426–444.

"Medical Applications of Ni–Ti Alloys in China", by Shibi Lu, M.D., pp. 445–451.

"An Operation for Stapling Vertebral Bodies in Congenital Scoliosis" by Alan D. Smith, William H. Von Lackum and Robert Wylie. *The Journal of bone and Joint Surgery*, vol. 36–A, No. 2, Apr. 1954 (pp. 342–348).

*Nickel–titanium Osteosynthesis Clips*, Bensmann, Baumgart, Haasters, Reprint from *Medical Focus*, 1983.

*Application of a NiTi Staple in the Metatarsal Osteotomy*, Tang, Dai, Chen, *Bio–Medical Materials and Engineering 6*, (1996) 307–312, IOS Press.

*Applications of Shape Memory Effects*, Besselink, Sachdeva, *Memory Metal Holland, Memory Medical Systems*, Publication date Unknown.

*The Use of a Memory Shape Staple in Cervical Anterior Fusion*, Ricart, *Proceedings of the Second International Conference on Shape Memory and Superelastic Technoloiges*, Asilomar Conference Center, Pacific Grove, CA, USA, 1997.

*Treatment of Intra–Articular Fractures with Shape Memory Compression Staples*, K.R. Dai, X.K. Hou, Y.H. Sun, R.G. Tang, S.J. Qiu and C. Ni, Injury, (1993) 24, (IO), 651–655.

*The Use of a Shape Memory Staple in Anterior Cervical Fusion*, Docteur Olivier Ricart.

*The Use of Sublaminar Cables to Replace Luque Wires*, Matthew N. Songer, MD, David L. Spncer, MD, Paul R. Meyer, Jr., MD and Gopal Jayaraman, PhD., Reprinted from *Spine*, vol. 16, No. 8S,Aug. 1991 Supplement, 1991®.

U.S. patent application Ser. No. 09/421,990, Hopf et al., filed Oct. 20, 1999.

*Spinal Surgery Before and After Paul Harrington*, Spine, Jun. 15, 1998, vol. 23, No. 12.

*Atlas of Spinal Operations*, Bauer, Kerschbaumer and Poisel, Thieme Medical Publishers, Inc., 1993, p. 160–162.

*Treatment of intra–articular Fractures with Shape Memory Compression Staples*, Dai, Hou, Sun, Tang, Qiu and Ni, International Journal of the Care of the Injured (1993) vol. 24/No. 10.

*The Use of a Shape Memory Staple in Anterior Cervical Fusion*, Docteur Olivier Ricart.

* cited by examiner

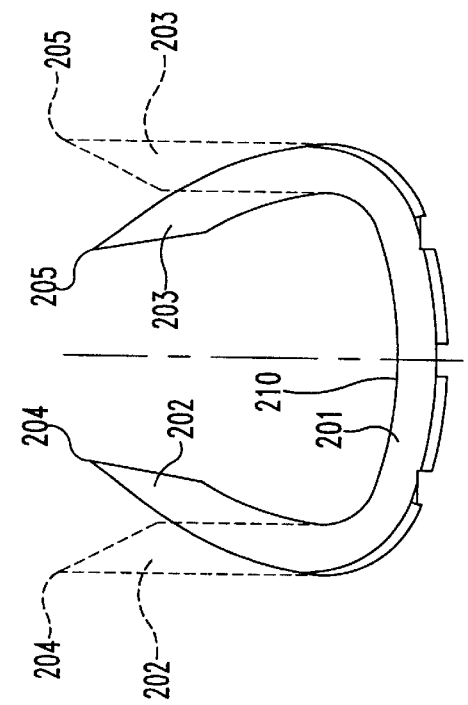
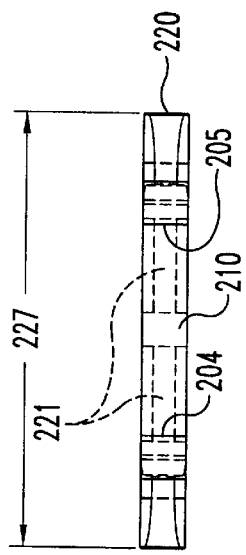
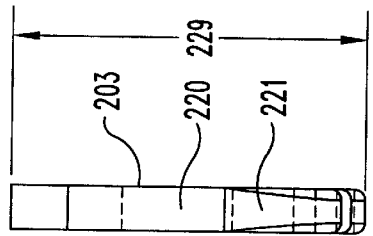
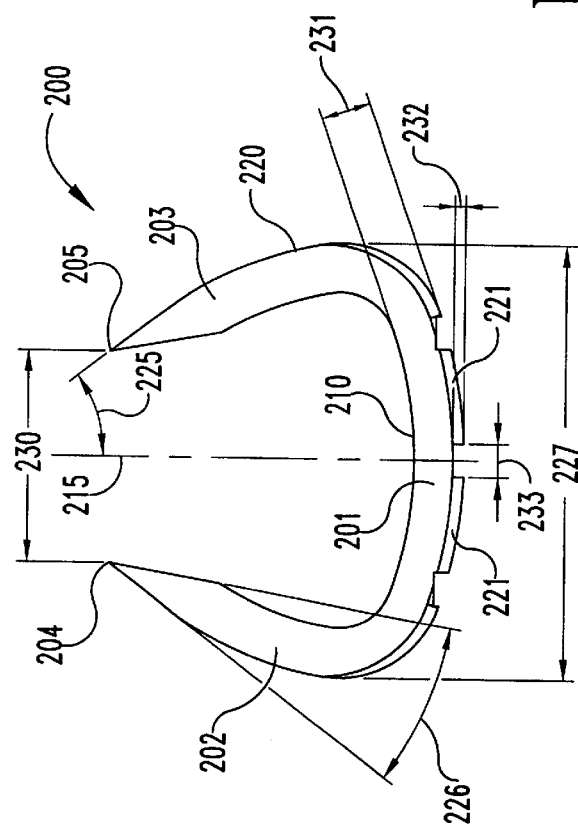

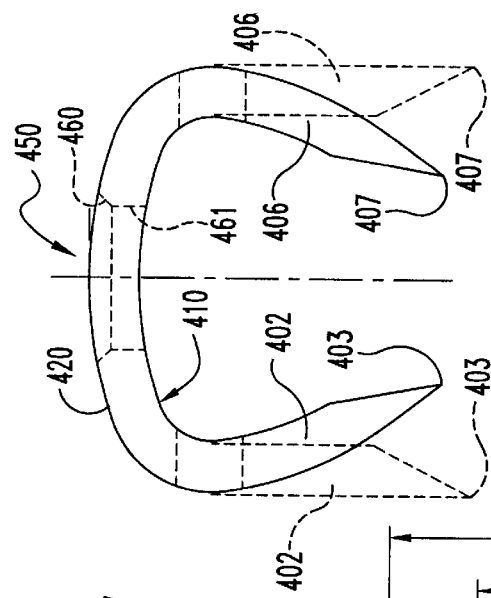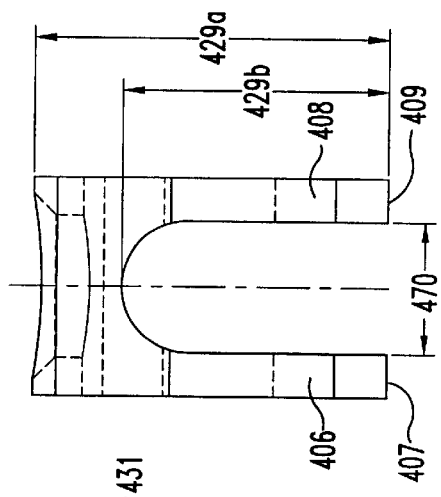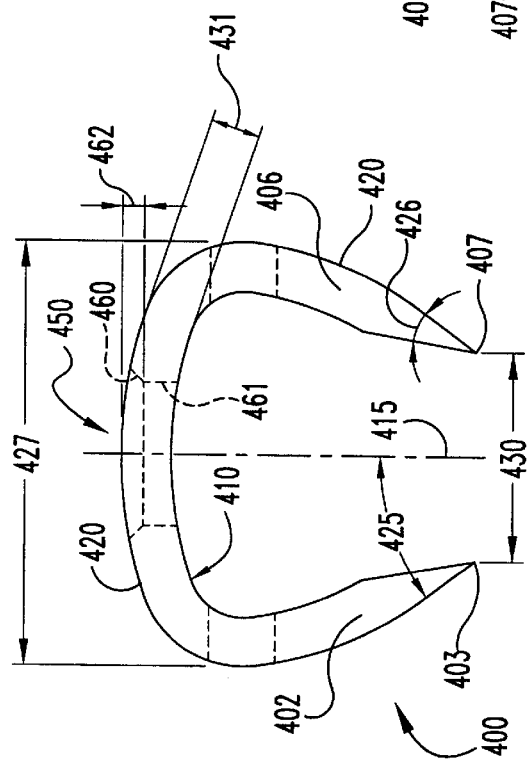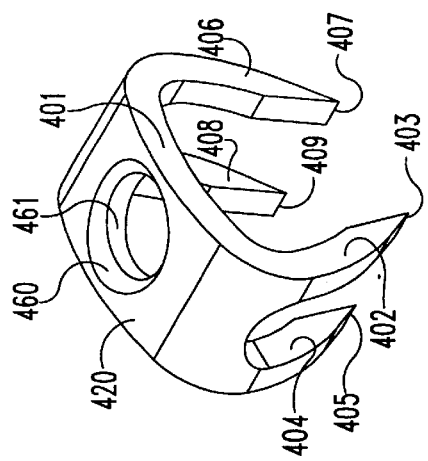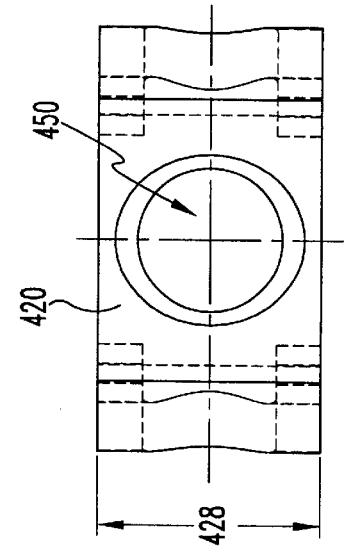
Fig. 15E
Fig. 15D
Fig. 15C
Fig. 15B
Fig. 15A

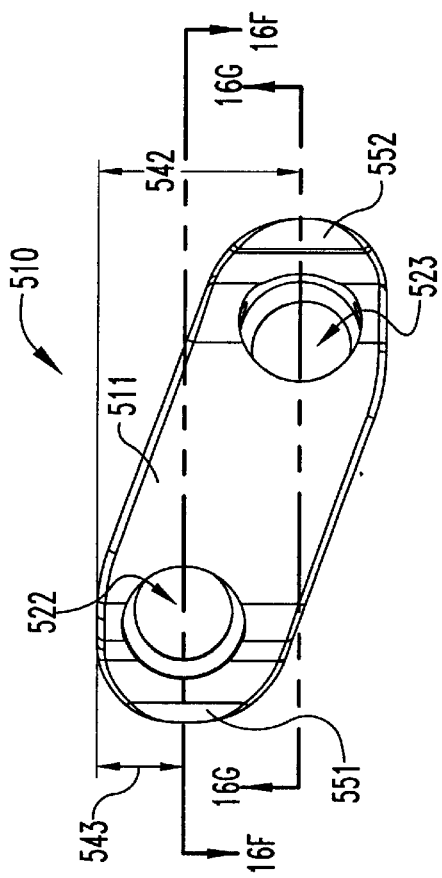
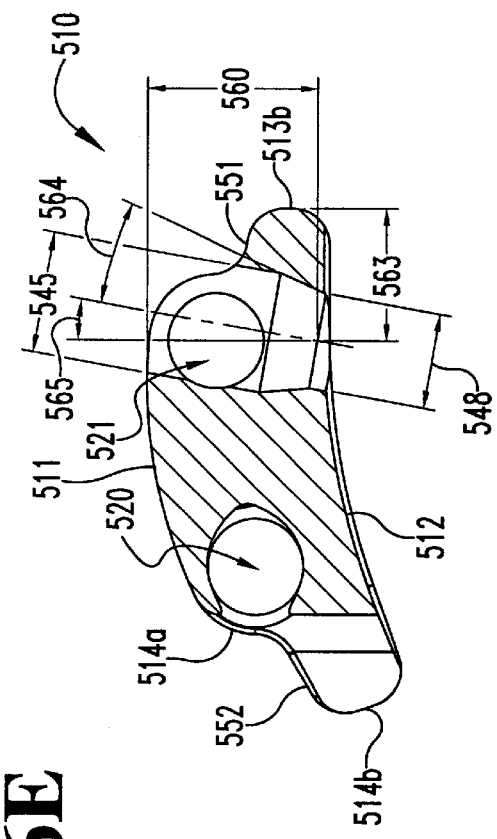
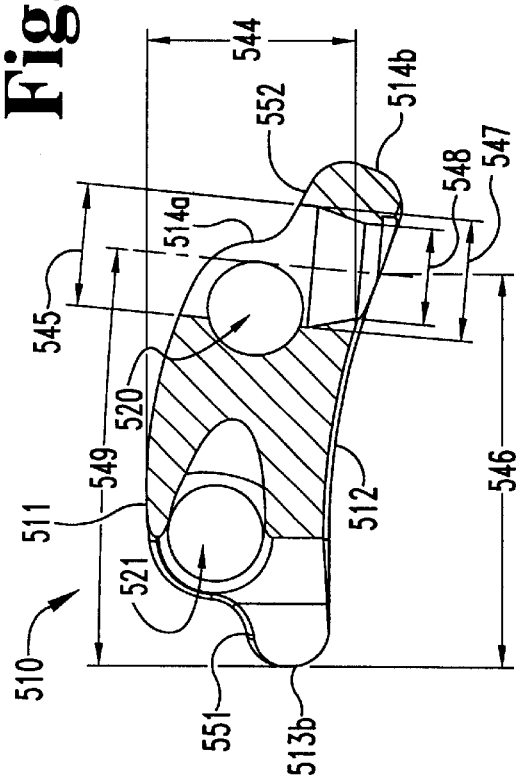

METHOD FOR THE CORRECTION OF SPINAL DEFORMITIES THROUGH VERTEBRAL BODY TETHERING WITHOUT FUSION

This application is a continuation of U.S. patent application Ser. No. 09/421,207, filed on Oct. 20, 1999, now U.S. Pat. No. 6,299,613, which claims the benefit of U.S. Provisional Patent Application No. 60/130,909, filed on Apr. 23, 1999, now abandoned.

BACKGROUND OF THE INVENTION

Current operative methods for treating spinal deformities, particularly scoliosis, include correction of the curve by some internal fixation device, and fusion of the spine in the corrected state usually accomplished by the placement of bone graft between vertebrae. This is usually accomplished with posterior surgery, although anterior procedures are becoming more popular, as well as combinations of anterior and posterior procedures. Several instrumentation systems are available from various manufacturers to correct and stabilize the spine while fusion occurs. Among them are TSRH®, CD™, CD Hopf™, CD Horizon™, ISOLA™, Moss Miami and Synthes Universal Spine Systems. Nonoperative methods do exist and are used when applicable. These nonoperative methods include bracing and observation.

Juvenile idiopathic scoliosis occurs between the ages of 4 and 10 years. It can resolve spontaneously, respond to nonoperative therapy, or progress until fusion is required. Stapling across long bone physes has long been recognized as a predictable method of treating limb malalignment. Vertebral interbody stapling across the cartilaginous endplates and discs was attempted by Nachlas and Borden in a canine scoliosis model. Early human results in the 1950s were disappointing. Roaf reported limited successful correction of scoliosis by uninstrumented convex hemiepiphysiodesis. His study did not have a uniform patient population by skeletal maturity or scoliosis etiology.

Further shortcomings of current operative methods and devices are numerous. Patients with juvenile scoliosis who undergo curve stabilization with subcutaneous rods would be subject to multiple surgical procedures for lengthening as they grow. Anterior and/or posterior spinal fusion in the skeletally immature patient often results in loss of vertebral body height and girth. Additionally, poor self-image may occur in adolescent patients who are braced for scoliosis. Moreover, curve stabilization with bracing is only successful in approximately 75% of patients. Another problem is that some children, while not currently candidates for a definitive fusion procedure, are likely to need such a procedure in the future. These would include children less than ten years of age, small in stature, premenstrual or riser two or lower, and those not physically able to tolerate the surgery required for a definitive fusion procedure. It would be preferable to eliminate the need for that procedure altogether.

SUMMARY OF THE INVENTION

Described briefly, one embodiment of the invention is a fusionless method of treating abnormal alignment of a spine of a child or a young adult. The spine has a convex side and a concave side. The method comprises the steps of attaching a tether to at least two vertebral bodies of the spine and then constraining curve progression in a portion of the convex side of the spine.

Another embodiment of the invention is a fusionless method of correcting deformities in a spine of a child or a young adult. The spine has a convex side and a concave side. The method comprises the steps of attaching a tether to at least two vertebral bodies of the spine and selectively constraining growth of the convex side of the spine.

Another embodiment of the invention is a device for restraining growth in a spine having a convex side and a concave side. The device comprises a strand, at least two blocks and a plurality of fasteners. Each block has a top surface, bottom surface and a first and second set of opposing side surfaces. The block is oriented on the spine so that the first set of side surfaces are located on an anterior part and a posterior part respectively of the spine. The block has a generally curved shape in a transverse direction from the anterior part to the posterior part corresponding to the antero-lateral anatomy of vertebral bodies. The bottom surface of the block is configured to contact a vertebral body. At least one fastener connects each block to at least one vertebra on the convex side of the spine. Each block has at least one channel for receiving the strand. Each block also has at least one bore extending between the top and bottom surfaces of the block. The bore receives one of the fasteners which connect the block to a vertebral body.

BRIEF DESCRIPTION OF THE DRAWINGS

FIG. 13A is a side view of another embodiment of a spinal staple.

FIG. 13B is a top view of the spinal staple of FIG. 13A

FIG. 13C is a side view of FIG. 13A.

FIG. 13D is a side view of the spinal staple of FIG. 13A with the insertion position shown in phantom.

FIG. 15A is a side view of another embodiment of a spinal staple of the present invention.

FIG. 15B is a top view of the embodiment of FIG. 15A.

FIG. 15C is another side view of the embodiment of the spinal staple of FIG. 15A.

FIG. 15D is a perspective view of the embodiment of FIG. 15A.

FIG. 15E is a side view of the embodiment of the spinal staple of FIG. 15A showing the times in the insertion position in phantom.

FIG. 16E is another top view of FIG. 16A illustrating further detail of the embodiment of the block.

FIG. 16F is a cross-sectional view along the line 16F in FIG. 16E.

FIG. 16G is another cross-sectional view of FIG. 16E along the line 16G.

DESCRIPTION OF THE PREFERRED EMBODIMENT

Figure 1:
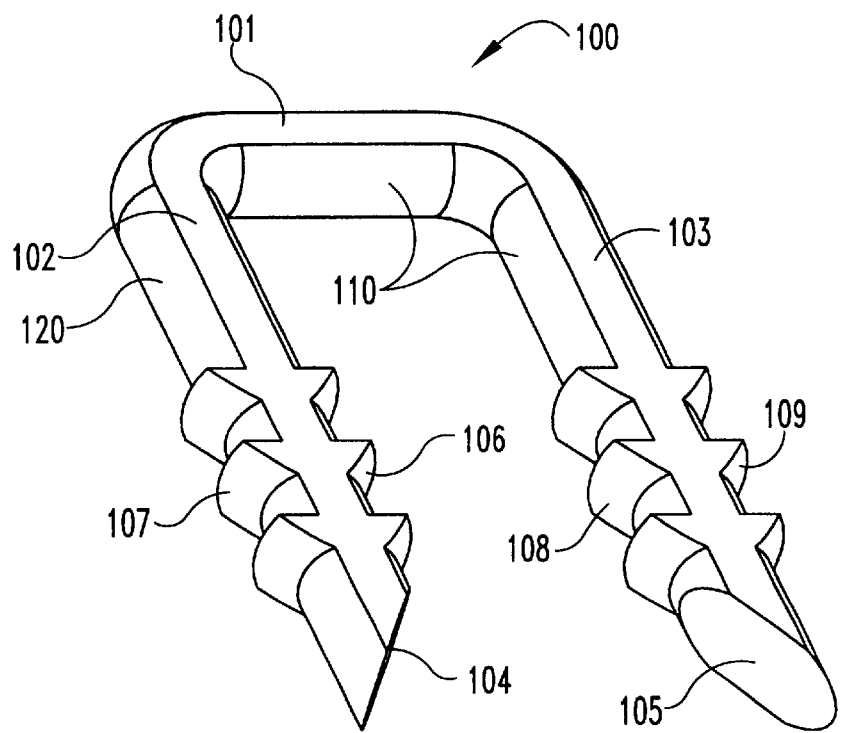
FIG. 1 is a perspective view of an embodiment of a spinal staple in accordance with this invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Various devices and surgical approaches are possible to implement the underlying idea of this invention. That idea is the correction of spinal deformities, particularly scoliosis, through fusionless tethering. The correction of the deformity is achieved by attaching a tether to the vertebral bodies on the convex side of the spine. This tether will minimize or arrest growth on the convex or "long" side of the spine and allow the concave or "short" side of the spine to grow and catch up with the long side. Alternatively, fusionless tethering may treat abnormal spinal alignment by simply preventing further misalignment such as curve progression.

A wide variety of surgical approaches may be used in implementing tethering of the convex side. One approach is an open thoracotomy (standard). Another surgical approach contemplated is a minimally invasive thoracoscopic approach (endoscopic). The surgical approach may also be a combined anterior/posterior approach (standard or endoscopic). It should be understood that the invention can be practiced using other surgical approaches known to persons of ordinary skill in the art.

In any surgical approach used in practicing the invention, the tether used to selectively constrain growth will include at least one longitudinal element and one anchor with an interconnection between the longitudinal element and the anchor. In some cases the longitudinal element and the anchor may be one and the same. The following discusses generally some of the types of apparatus that may be used. Additionally, it should be understood that most, if not all, of the longitudinal elements or anchors may be manufactured from, but are not limited to, conventional implant metals, such as stainless steel or titanium. It should be further understood, and will be discussed in some detail for particular embodiments, that the longitudinal elements and anchors may take advantage of the shape memory and superelastic characteristics of shape memory materials including, for example, a shape memory alloy ("SMA") such as nickel titanium.

Several devices are contemplated for spanning the longitudinal aspect of the spine during the fusionless tethering procedure. A list of potential longitudinal elements includes, but is not limited to, staples, cables, artificial strands, rods, plates, springs, and combinations of devices from the foregoing list. Details of each individual element will be discussed briefly.

The longitudinal element may be a spinal staple formed in a variety of shapes and sizes depending on its application. Staples may act as either the longitudinal element, the anchor, or both. These staples may be manufactured from conventional implant metal, such as stainless steel or titanium. In one preferred embodiment, however, the staples are manufactured out of shape memory materials or alloys such as nickel titanium to enhance fixation. One example of such an alloy is Nitinol sold by Memry Corporation of Menlo Park, Calif. Further details of preferred use, size, and material selection for the spinal staple maybe found in copending patent application U.S. Ser. No. 09/421,903, entitled "Shape Memory Alloy Spinal Staple" filed on the same day as the present application and commonly assigned to the assignee of the present application, the disclosure of which is incorporated herein by reference.

Another possible selection for the longitudinal element is cabling. Historical spinal instrumentation involved the use of cables (Dwyer) as a fixation method for spinal fusion. However, this use of cable never contemplated that a flexible cable could represent the longitudinal element in a fusionless tethering procedure.

The use of artificial or synthetic strands, much in the same way cable could be used, may potentially add additional flexibility and motion to this fusionless tethering procedure. In one preferred embodiment the artificial strand may be manufactured from a braided polymer rope. In another preferred embodiment the artificial strand will be an adjustable spinal tether. Details of various embodiments of the adjustable spinal tether may be found in provisional patent application U.S. Ser. No. 60/130,910, entitled "Adjustable Spinal Tether" filed on Apr. 23, 1999 and commonly assigned to the assignee of the present application, the disclosure of which is incorporated herein by reference. Such an artificial strand is preferably (but not necessarily) used in conjunction with a block similar or identical to various embodiments of the "Hopf blocks" disclosed in U.S. Pat. No. 5,702,395 to Hopf entitled "Spine Osteosynthesis Instrumentation for an Anterior Approach" the disclosure of which is incorporated herein by reference. It is contemplated as within the scope of the invention, however, that the artificial strand may be utilized for fusionless tethering in a variety of manners. These include, but are not limited to, being attached to or around anchors such as screws and staples. It is further contemplated as within the scope of the invention that the artificial strand may also act as both the longitudinal element and the anchor by being secured directly around the vertebrae to be tethered.

Another possible selection for the longitudinal element is a flexible rod. These could be manufactured of small diameter and/or flexible material such as a super elastic SMA. In a similar manner plates may be used as a longitudinal element. The plates can be used with or without slots allowing implants to slide. Another possible choice is a spring. Springs have been used historically in spinal instrumentation and could form the longitudinal element. Again, to reiterate, it should be understood that combinations of any or all of the above may be used as a longitudinal element when deemed appropriate.

Most of the longitudinal elements discussed above, the staples and artificial strands being possible exceptions, will need to be anchored to the vertebral bodies in order to effectively tether them. Several different anchors are contemplated.

As previously mentioned, staples can be both anchors, as well as longitudinal elements since they possess the characteristics of both. These staples can be either conventional or a SMA as stated above. Also available for use in this capacity are scaled up suture anchor type products. Novel approaches using such products known in the art are available to fix to soft cancellous bone such as that found in a vertebral body. Additionally, screw down fixation plates, posts, etc. as are known to those of ordinary skill in the art, may be used as anchors.

Another potential anchor is an expandable screw. Examples include Mollie bolt type implants that are initially screwed into the vertebral body and expand through some mechanism. It is again possible to take advantage of the properties of shape memory materials to accomplish the expansion mechanism. Conventional screws and bone screws may also serve as anchors. These screws may be coated with any number of osteoinductive or osteoconductive materials to enhance fixation as desired.

The selection of the longitudinal elements and anchors from those previously discussed and others known in the art also leaves possible the selection of a wide variety of interconnections between the two. Once the anchors are in place, their connection to the longitudinal elements can be governed by a number of different parameters. They could be constrained or unconstrained connections; the anchor could be allowed to slide along the longitudinal element or articulate with it, as in the case of a ball joint, or even float within some neutral zone. Several scenarios are envisioned.

The first is constrained. This would involve constrained interconnection scenarios between all anchors and longitudinal elements. The second is un-constrained. This would involve simple connections in which no significant restrictions exist between the longitudinal element and the anchor. An example is an artificial strand band around a post, or a screw through an artificial strand ribbon.

The third scenario is ends constrained with middle elements un-constrained. In this case the construct would possess constrained interconnections between the end anchors and the longitudinal elements with unconstrained interconnections in between. These unconstrained interconnections could be either sliding situations or ball joint situations. The fourth scenario is ball joint interconnections. Ball joints represent a semi-constrained situation in which the anchor cannot slide up or down the longitudinal element, but can articulate within some spherical range of motion. It should be understood that combinations of any or all of the above may be used as appropriate in practicing the present invention.

The above disclosure deals specifically with the broad range of device concepts envisioned for fusionless tethering of deformities in order to achieve permanent correction. The specifics with regard to the method are similarly broad. A wide range of spinal deformities could be managed. The primary indications will be progressive idiopathic scoliosis with or without sagittal deformity in either infantile or juvenile patients. The preferred patient population upon which to practice the present invention is prepubescent children (before growth spurt) less ,than ten years old. Other patient groups upon which the present invention may be practiced include adolescents from 10–12 years old with continued growth potential. It should be understood that fusionless tethering may be used on older children whose growth spurt is late or who otherwise retain growth potential. It should be further understood that fusionless tethering may also find use in preventing or minimizing curve progression in individuals of various ages.

Generally, in the case of scoliosis, tethering will take place on the convex side of the curve. An anterior, minimally invasive (thoracoscopic) procedure can be carried out on the convex side of the spinal curve in order to prevent continued growth on that side of the curve. As the pre-growth spurt child approaches puberty, the untethered side of the spine will grow unconstrained, ultimately eliminating the curvature of the spine in the frontal plane. It is preferable to deliver this method of treatment in a minimally invasive approach using thoracoscopic instrumentation. It is contemplated as within the scope of the invention, however, that open use of these systems may be appropriate in some cases. It is further contemplated as within the scope of the invention that the procedure may be posterior as well as anterior, or some combination of both. Finally, it should be understood that if the procedure fails to correct the curve but does, in fact, prevent further progression (which includes increase in the magnitude of the curve) it can and should be considered successful.

EXAMPLE ONE

Thoracoscopic Assisted Spine Stapling.

In one embodiment of the invention, fusionless correction of scoliosis is achieved by thoracoscopically placing shape memory alloy staples into the vertebral bodies on the convex side of the spine. The staples will span the intervertebral space and act as a tether on the spine. This tether will arrest growth on the convex ("long") side of the spine and allow the concave ("short") side of the spine to grow and catch up with the long side. Once correction is achieved, the staple may then be removed thoracoscopically if desired. The removal of the staples permits further growth of the vertebral bodies. It should be understood that the method described is equally applicable in non-endoscopic procedures. It should be further understood that the staples used may be made of a conventional implant metal such as titanium or stainless steel instead of a SMA.

The following contraindications for use of thoracoscopically assisted spinal stapling should be noted: (1) Inability to wear an orthosis postoperatively, (2) Greater than 40 degree kyphosis, (3) Medical contraindication to general anesthetic, (4) Pulmonary function which would contraindicate intraoperative collapse of the convex lung, and (5) Scoliosis deformity where three or more disc spaces are not accessible to thoracoscopically assisted vertebral interbody stapling. It should be understood, however, that the presence of any or all of the above mentioned contraindications does not preclude the potential utility of spinal stapling and/or vertebral body tethering.

The general details of one embodiment of the surgical technique would be as follows. General anesthesia is utilized. A double lumen endotracheal tube is inserted, with possible assistance of fiberoptic visualization. The convex, lung is collapsed. A general or vascular surgeon familiar with endoscopic surgery in the thorax may be used as an assistant. The patient is positioned in the lateral decubitus position with the convex side of the scoliosis in the up position. The table is not flexed Five vertebrae (four intervertebral discs) are usually stapled. The apical vertebral body, the two vertebrae proximal, and the two vertebrae distal are treated. Three endoscopic ports are utilized. The first port is anterior and positioned over the apex of the scoliosis. The second and third ports are made in the posterior auxiliary line with the second port being centered over the second vertebrae of the five being treated and the third port being centered over the fourth vertebrae being treated. The endoscope is maintained in the first port and a fan retractor is placed in the second port. An anterior-posterior (AP) radiograph is used to confirm the levels. The parietal pleura is not excised and the segmental vessels are avoided.

A number of general surgical instruments are used in the procedure along with the following system specific implants and instruments. The main implant is of course a spinal staple, preferably manufactured from a shape memory material. The size will vary depending on the size and number of the vertebral bodies to be spanned. The instruments used in the procedure may also include: Staple Awl, Staple Opener, Straight Staple Inserter, Angled Staple Inserter, Staple Impactor, Staple Extractor.

Pilot holes are made using the Staple Awl. The pilot holes are made anterior to the midbody of the vertebrae. The Staple Awl is inserted part way and position is checked with either x-ray or image intensifier. Prior to removal of the Staple Awl from the pilot holes, an electric cauterizer (Bovie) can be placed in contact with the endcap of the Staple Awl to minimize bleeding from the pilot holes. In one preferred embodiment, two sets of pilot holes are made at each level to accommodate two staples per disc space. Two staples are then placed spanning each disc space. The first staple is loaded into either the Straight Staple Inserter or, the Angled Staple Inserter. The staple is then placed into the pilot holes previously made with the Staple Awl. The Inserter may be tapped with a mallet to facilitate placement of the staple. The staple is then released from the Inserter and then the instrument is removed. If further seating of the staple is required, the Staple Impactor may be used in conjunction with a mallet for final seating of the staple into the bone. The aforementioned steps are repeated for the next staple at that spinal level. It should be understood, however, that tethering may also be accomplished with just one staple instead of two spanning each disc space. It should be further understood that the use of more than one staple allows for correction of spinal curvature in more than one plane.

The instruments in the second and third ports are switched and the remaining two discs are stapled. The wounds are closed and a ten or twelve gauge chest tube is inserted which is withdrawn at twenty-four hours postop. The chest tube is used to prevent pneumothorax since there is no hemothorax. Once the endoscope is in place, the remainder of the procedure seldom takes more than one hour. Hospitalization is usually for two to three days.

Apical vertebral interbody stapling theoretically affords immediate and reversible fixation of the anterior vertebral physes. Thoracoscopic insertion minimizes damage to surrounding tissues and permits placement of multiple staples to allow curve correction in more than one plane.

Figure 2:
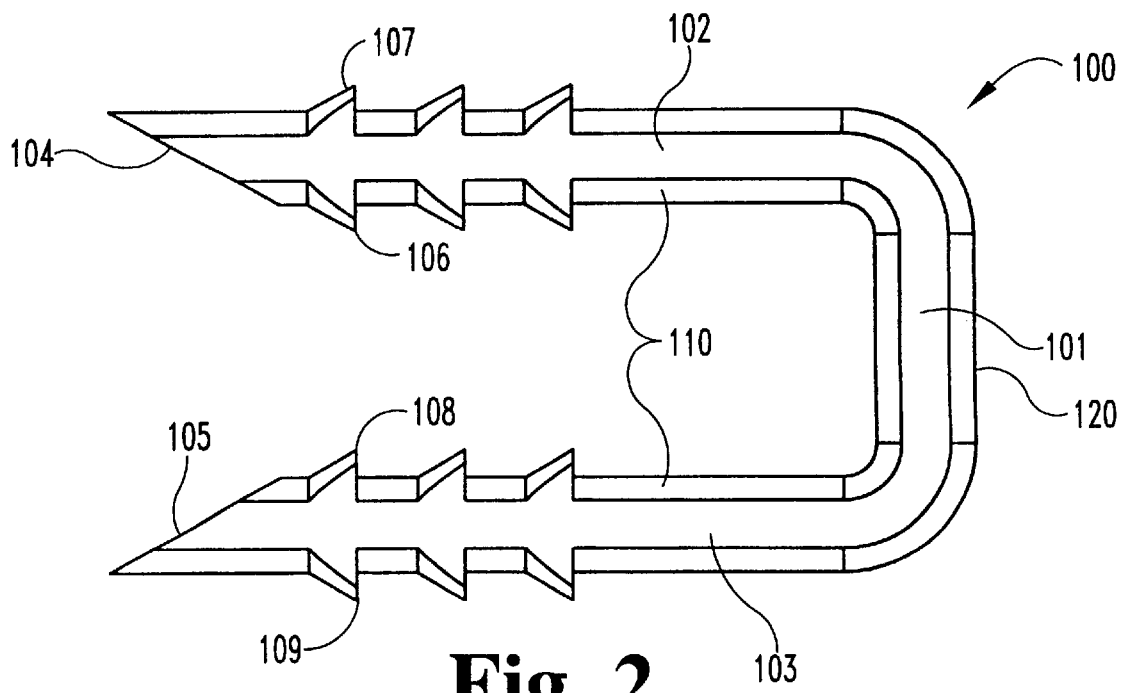
FIG. 2 is a side view of the spinal staple of FIG. 1.

With reference to FIGS. 1 and 2, one embodiment of an vertebral interbody staple 100 that may be used in the above described method is shown. Staple 100 is generally U-shaped with crossbar 101 between legs 102 and 103. Staple 100 has inner surface 110 and outer surface 120. Leg 102 has a pointed tip 104 and leg 103 has a pointed tip 105 for insertion into the vertebral bodies. It should be understood that tips 104, 105 may have a variety of configurations. Leg 102 has barbs 106 on inner surface 110 and barbs 107 on outer surface 120. Similarly, leg 103 has barbs 108 on inner surface 1 10 and barbs 109 on outer surface 120. Barbs 106, 107, 108, and 109 aid in the prevention of staple backout. Having barbs on both inner surface 110 and outer surface 120 of each leg 102, 103 of staple 100 allows the use of shorter barbs in the direction transverse to the longitudinal axis of each leg. It should be understood, however, that each leg 102, 103 may only have barbs on the inner surface 1 10 or outer surface 120.

It should be noted that in one preferred embodiment crossbar 101, and legs 102 and 103 all have a nearly elliptical profile obtained by truncating a circular cross-section. A staple design with an elliptical or near elliptical crossbar 101 is helpful in controlling rotation of the staple 100 and permits some assistance in staple removal. It should be understood that the profile of legs 102, 103 and crossbar 101 may be other than elliptical, such as a circular cross-section. It should be further understood that legs 102, 103 and connecting portion 101 may have different profiles. The staple design of FIGS. 1 and 2 may be made of commercially pure titanium, some other conventional implant metal, or even a SMA.

While details of several embodiments of the staple are discussed in the copending application titled "Shape Memory Alloy Spinal Staple," some general points are reviewed here for convenience. The staples are preferably made of nitinol, a biocompatible, shape memory metal alloy of titanium and nickel. Staples are capable of being bent when cooled and reform to their original shape when reheated. It is also possible to take advantage of the shape memory alloy's ability to transform from its austentic state to a stress induced martensitic state. The metal changes shape with temperature or under the influence of stress because of crystalline phase changes. Thus a staple made of a SMA can be inserted in two different ways as desired. In one embodiment the SMA staple is cooled and then deformed while at a temperature less than the transformation temperature at which it is in the martensitic phase. The staple is then inserted in its deformed shape and when heated will reform to its original shape. In a second embodiment the staple is deformed and inserted while held in the deformed state. In the second embodiment the SMA is selected to have a temperature transformation range such that the staple undergoes a transition from austenite to stress-induced martensite under the influence of the deformation forces. Thus, when the staple of the second embodiment is inserted and released it is already at a temperature such that it automatically attempts to reform to its original shape.

The metal's properties at the higher temperature (austenite phase) are similar to those of titanium. The temperature at which the staples will undergo the shape transformation can be controlled by the manufacturing process and the selection of the appropriate alloy composition. Injury to the surrounding tissues should be negligible if the transformation temperature is near body temperature. There is no threat of thermal injury to the spinal cord or nerves, or adjacent vascular structures. Nitinol has a very low corrosion rate and has been used in a variety of medical implants (i.e., orthodontic appliances, stents). Implant studies in animals have shown minimal elevations of nickel in the tissues in contact with the metal; the levels of titanium are comparable to the lowest levels found in tissues near titanium hip prostheses.

EXAMPLE TWO

Blocks With Cabling or Synthetic Strands

Another device useful for correction of spinal deformities through fusionless tethering involves the use of blocks similar or identical to those disclosed in the above mentioned U.S. Pat. No. 5,702,395 to Hopf titled "Spine Osteosynthesis Instrumentation for an Anterior Approach" along with cabling or artificial strands. Several preferred embodiments for use as an artificial strand are disclosed in the above mentioned provisional patent application U.S. Ser. No. 60/130,910 entitled "Adjustable Spinal Tether."

Figure 3:
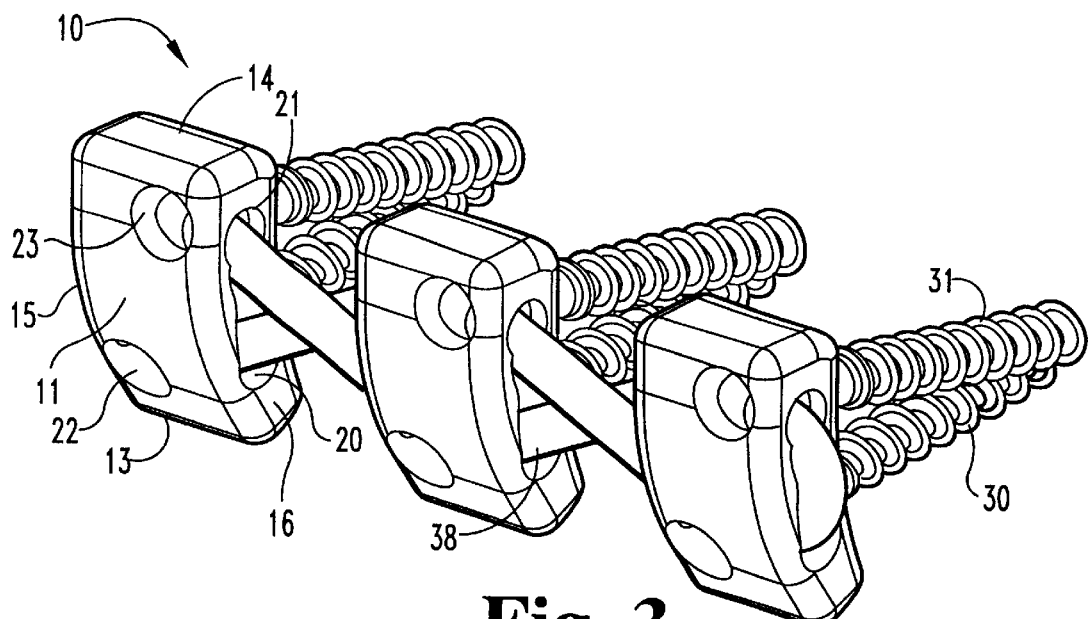
FIG. 3 is a perspective view of an embodiment of a tether of the present invention including a set of blocks and fasteners with a strand threaded through channels in the blocks.
Figure 4:
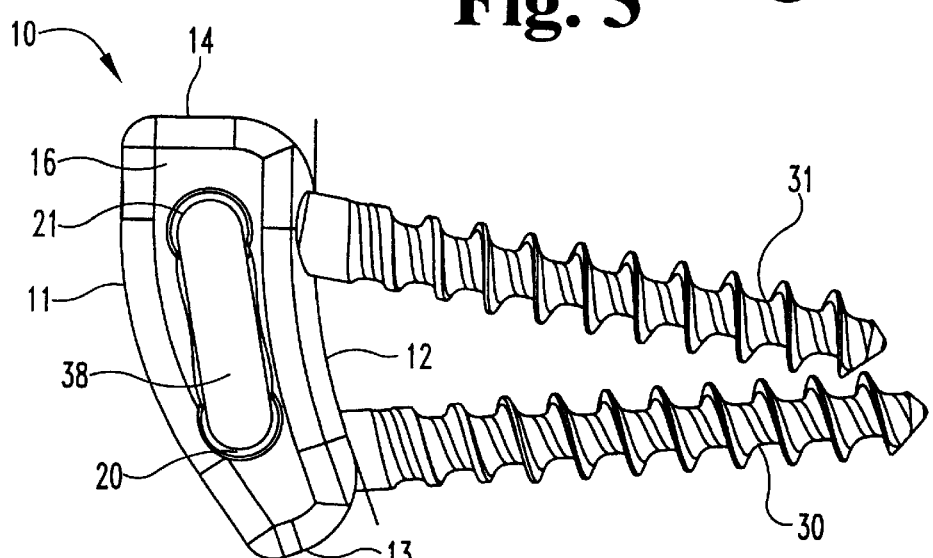
FIG. 4 is a side view of the embodiment of FIG. 3.

With reference to FIGS. 3 and 4, one embodiment includes a set of three blocks with corresponding fasteners and a synthetic strand or cable threaded through channels in the blocks is shown. It should be understood that anywhere from two to greater than five blocks may be used. In one preferred embodiment the number of blocks is three. Each block 10 has a top surface 11 and a bottom surface 12 along with first and second sets of opposing side surfaces. The block 10 is oriented so that in the first set, side surfaces 13, 14 are located on an anterior and a posterior part respectively of the spine (see also FIGS. 8 and 9). The block 10 has a generally curved shape in a transverse direction from the anterior surface 13 to the posterior surface 14 corresponding to the antero-lateral anatomy of vertebral bodies. The bottom surface 12 is configured to contact a vertebral body.

Each block 10 has a second set of side surfaces 15, 16 which are oriented substantially upward and downward along the longitudinal axis $S_k$ of the spine (see FIGS. 8 and 9). The upper surface 15 and lower surface 16 of each block 10 define at least one opening or channel for receiving synthetic strand 38. In an embodiment with only one channel, the channel must either have a post or divider somewhere along its length around which the strand 38 is wrapped or else the strand 38 may be threaded through the channel and around either the top surface 11 or bottom surface 12 of each block 10. In one preferred embodiment (see FIG. 3), each block 10 has two substantially parallel channels, an anterior channel 20 and a posterior channel 21. Anterior channel 20 and posterior channel 21 extend in a direction along a line connecting upper surface 15 and lower surface 16. It is contemplated as within the scope of the invention that anterior channel 20 and posterior channel 21 may extend in different directions and/or be curved in between upper surface 15 and lower surface 16. It is further contemplated as within the scope of the invention that anterior channel 20 and posterior channel 21 may be at an angle with respect to either or both of upper surface 15 and lower surface 16. Moreover, channels 20 and 21 may both be closer to anterior surface 13 than posterior surface 14 or vice versa. Selection of various channel orientations permits configurations for the synthetic strand other than the figure eight or straight loop configuration discussed below. Also, it should be understood that the channels such as 20 and 21 may instead connect the first set of opposing side surfaces 13 and 14 or may connect some combination of the first and second sets of opposing side surfaces.

Additionally, each block 10 further defines at least one bore extending between top surface 11 and bottom surface 12. Each block 10 may have one or more bores for receiving a fastener to connect each block to a vertebral body. In one preferred embodiment block 10 has two bores, an anterior bore 22 and a posterior bore 23. It should be understood that each block 10 may have only one bore or more than two depending on the number of fasteners a surgeon wishes to use to attach each block to a vertebral body. Each bore 22, 23 extends between the top surface 11 and bottom surface 12 of block 10. Bores 22, 23 are defined in block 10 with dimensions such that each bore may receive one of the fasteners used to attach the block 10 to the vertebral body.

Figure 10A:
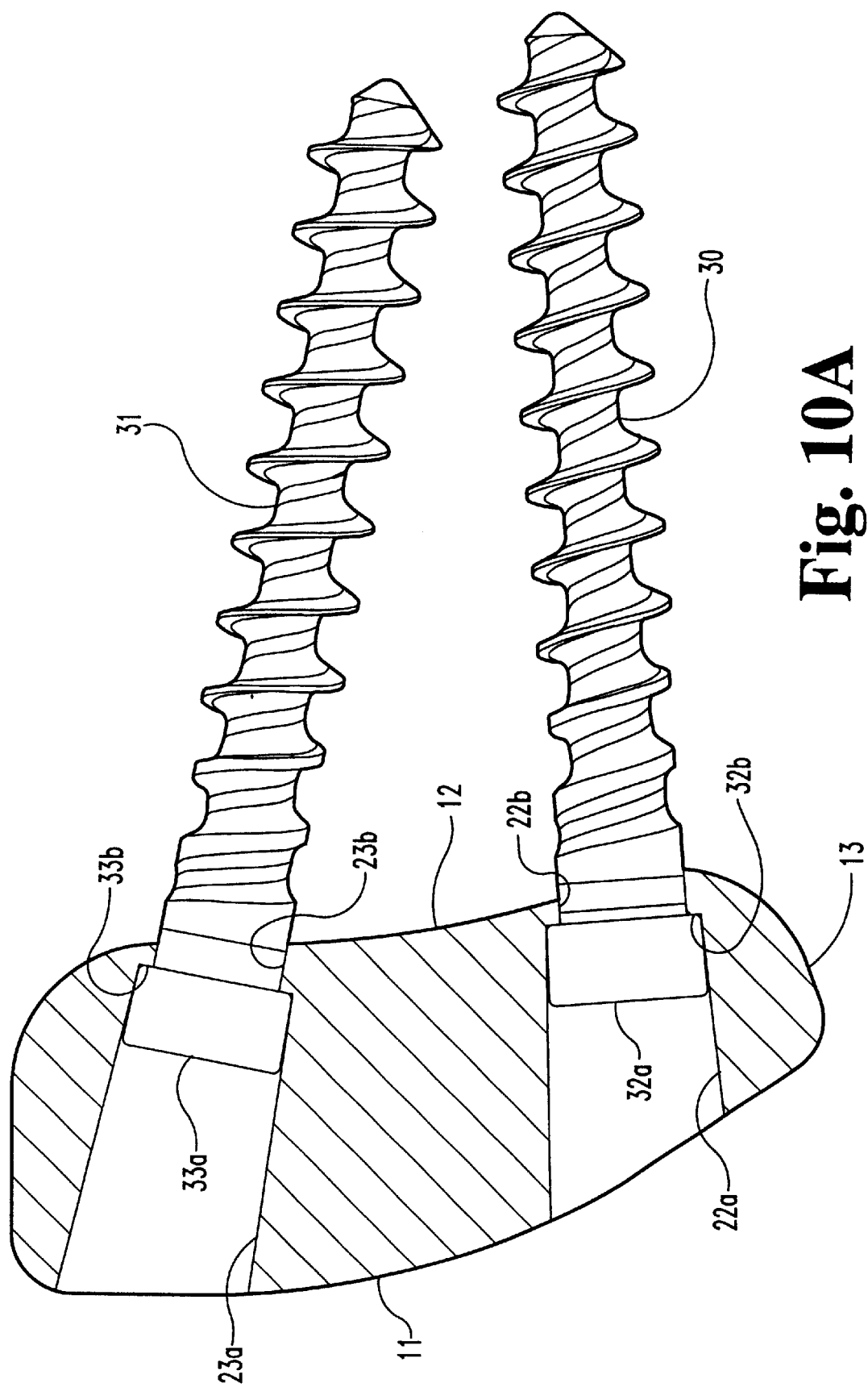
FIG. 10A is a cross-sectional view of one embodiment of the interconnection between the fasteners and the blocks.

The bottom portion of bores 22, 23 near bottom surface 12 are preferably sized to snugly receive the heads 32, 33 of fasteners 30, 31. With reference to FIG. 10A in which like elements are labeled as previously, it is seen that bore 22 has a top portion 22a and bottom portion 22b. Similarly bore 23 has a top portion 23a and a bottom portion 23b. Top portions 22a and 23a are preferably (but not necessarily) tapered for facilitating insertion of fasteners 30, 31 through bores 22, 23 respectively. The head 32 of fastener 30 has a top portion 32a with a notch therein for receiving a driving mechanism and a bottom portion 32b configured to engage the bottom portion 22b of bore 22. Similarly, the head 33 of fastener 31 has a top portion 33a with a notch therein for receiving a driving mechanism and a bottom portion 33b configured to engage the bottom portion 23b of bore 23.

Figure 10B:
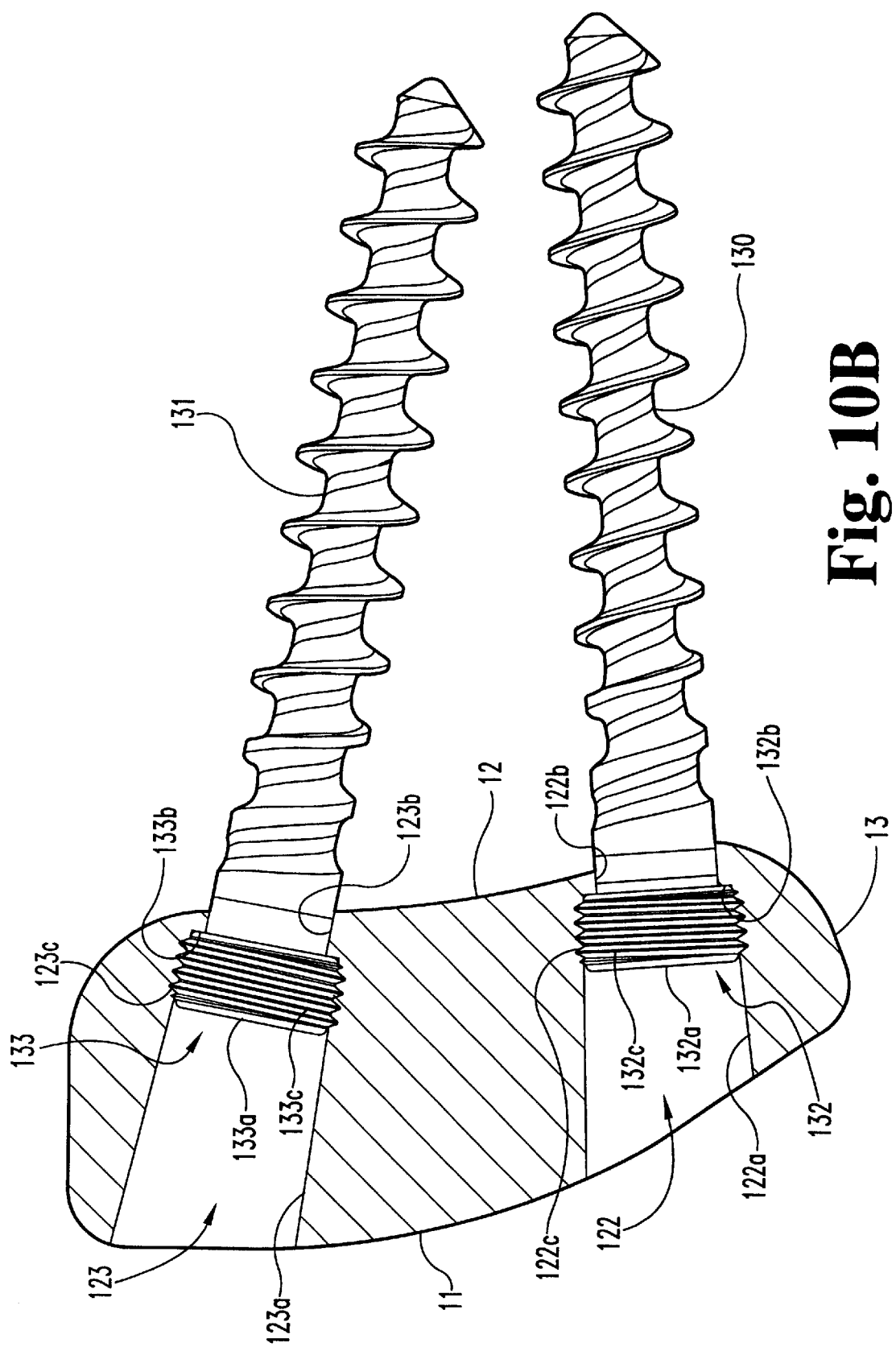
FIG. 10B is a cross-sectional view of another embodiment of the interconnection between the fasteners and the blocks having a screw back-out mechanism.

With reference to FIG. 10B, an alternative embodiment is shown with a mechanism to aid in the prevention of screw back out. With reference to FIG. 10B, in which like elements are labeled as previously, it is seen that bore 122 has a top portion 122a and bottom portion 122b. Similarly, bore 123 has a top portion 123a and a bottom portion 123b. Top portions 122a and 123a are preferably (but not necessarily) tapered for facilitating insertion of fasteners 130, 131 through bores 122, 123 respectively. The head 132 of fastener 130 has a top portion 132a with a notch therein for receiving a driving mechanism and a bottom portion 132b configured to engage the bottom portion 122b of bore 122. Similarly, the head 133 of fastener 131 has a top portion 133a with a notch therein for receiving a driving mechanism and a bottom portion 133b configured to engage the bottom portion 123b of bore 123. The head 132 of fastener 130 has external threading 132c defined thereon which engages threading 122c defined in bore 122 and aids in the prevention of screw back out. Similarly, the head 133 of fastener 131 has threading 133c defined on the head 133 which engages threading 123c defined in bore 123.

Figure 11:
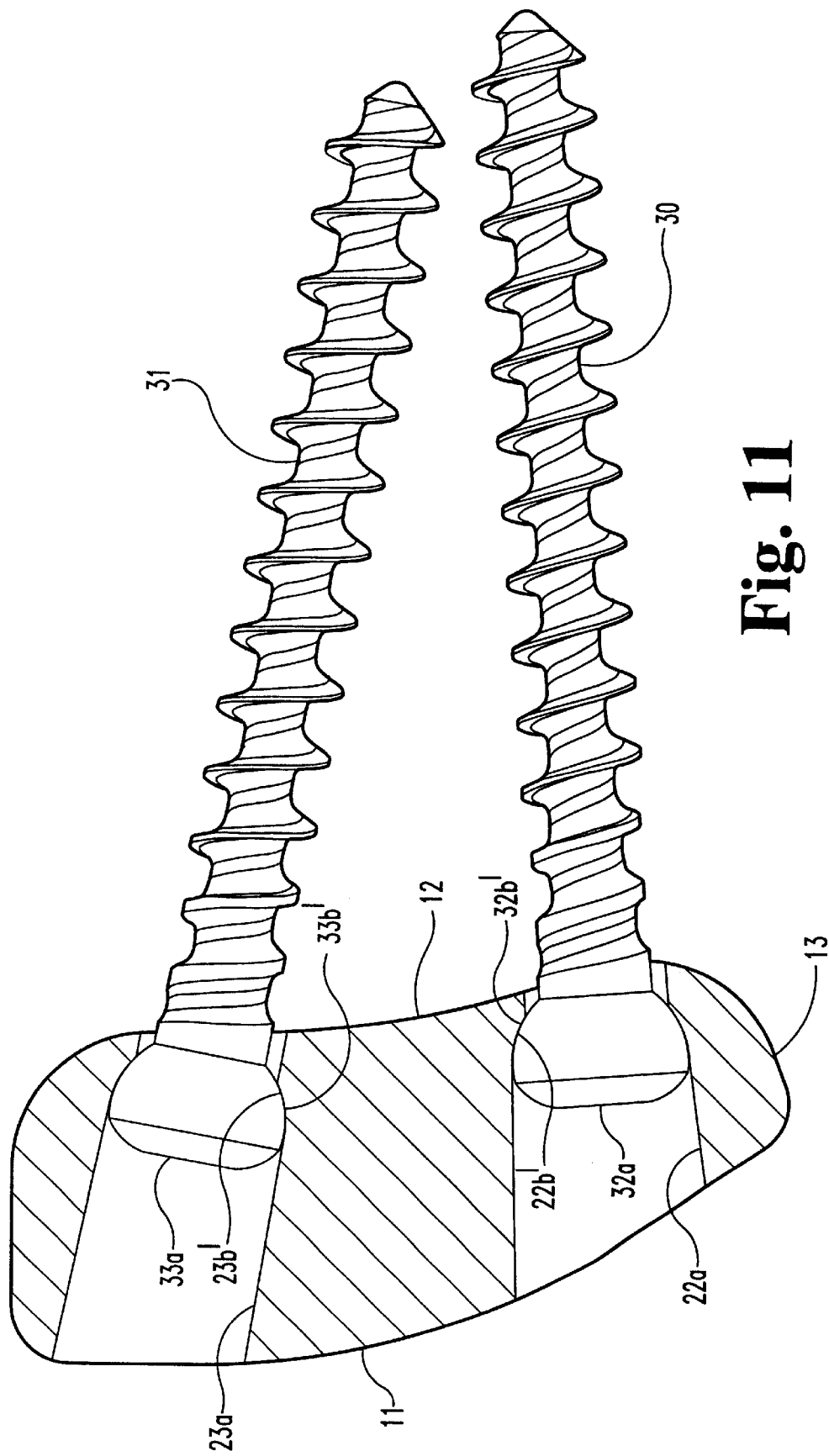
FIG. 11 is a cross-sectional view of another embodiment of the interconnection between the fasteners and the blocks.

It should be understood that bores 22, 23 may also be sized to loosely receive heads 32 and 33. The bottom portion of bores 22, 23 and heads 32, 33 may both be shaped for ball and socket interconnection allowing the pivoting or swiveling of the connecting portion of fasteners 30, 31 relative to each block 10. With reference to FIG. 11 in which like elements are labeled as previously, the bottom portions 32b', 33b' of heads 32,33 are hemispherical as are the bottom portions 22b', 23b'. Again the top portions 22a, 23a are preferably tapered to facilitate insertion of the fasteners through the bores. Alternatively, in another embodiment the bores 22, 23 and heads 32, 33 may be shaped for engagement such that the angle of the fasteners 30, 31 with respect to each other and the block 10 is substantially fixed. It should be understood that in either case, it may be desirable in some situations to use a screw back out system as described with reference to FIG. 10B or others known in the art.

In one embodiment, bore 22 intersects with channel 20 and bore 23 intersects channel 21. It should be understood, however, that the bores 22, 23 need not intersect channels 20, 21. In the embodiment where the bores 22, 23 intersect the channels 20, 21, each bore is preferably defined in such a manner that the top of heads 32, 33 of fasteners 30, 31 are not within channels 20, 21 when fasteners 30, 31 are in the bottom portion of bores 22, 23 (see FIGS. 5, 8, and 9). As a result, strand or cable 38 is unobstructed when threaded through channels 20, 21.

Figure 5:
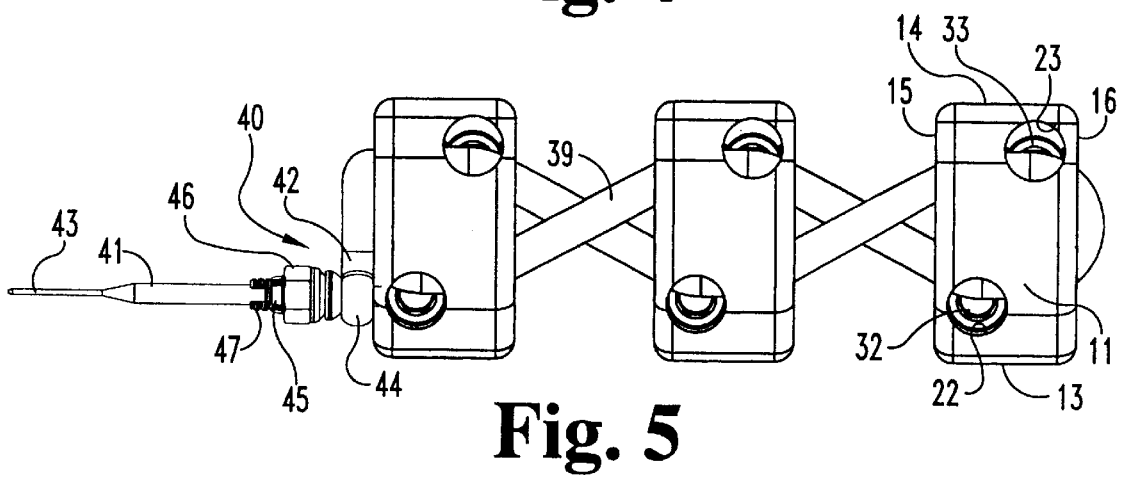
FIG. 5 is a top view of an alternative to the embodiment of FIG. 3 where the strand is an adjustable spinal tether in a figure eight configuration.
Figure 8A:
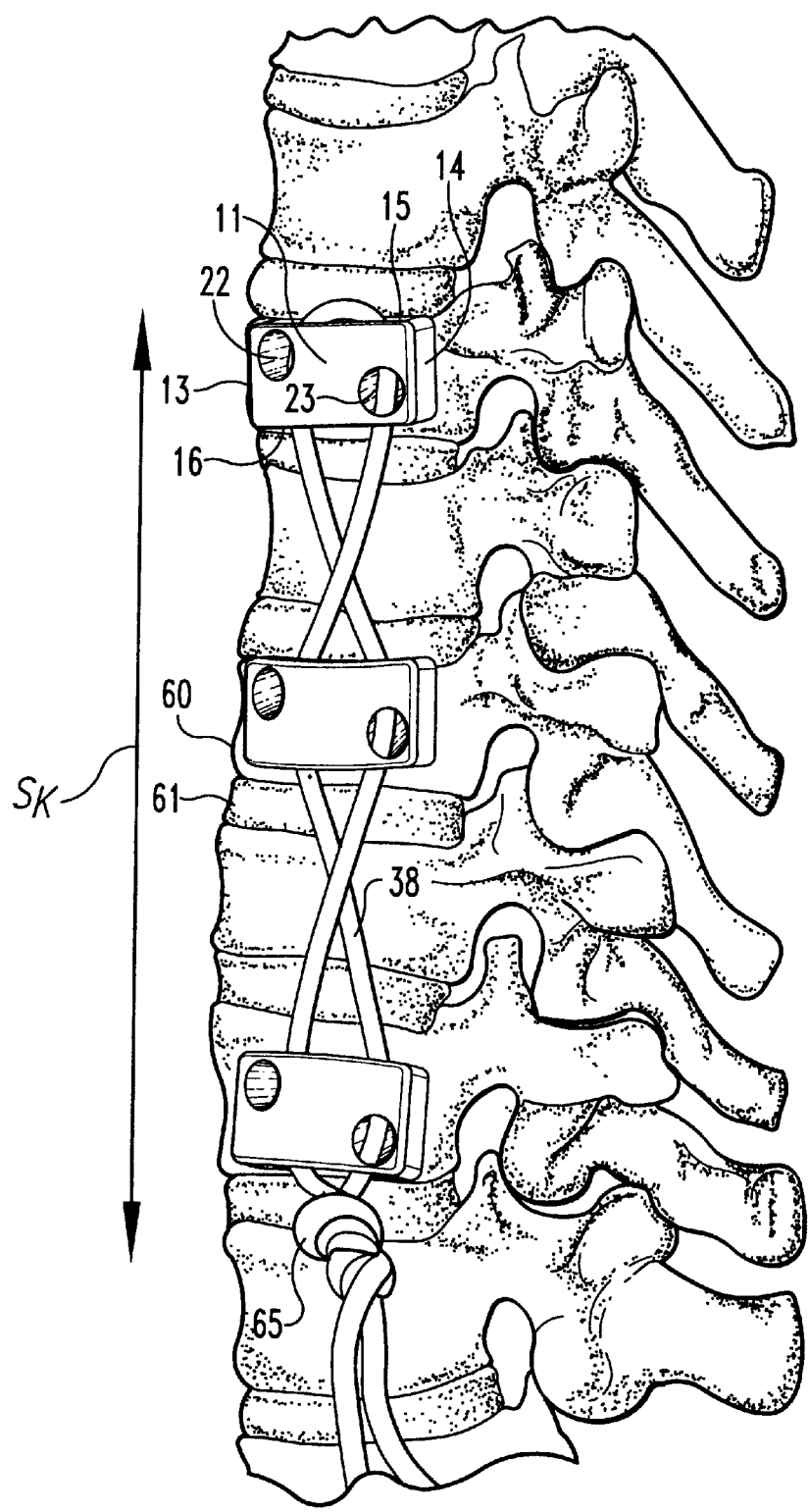
FIG. 8A is a schematic illustration of the embodiment of FIG. 3 attached to vertebral bodies on the convex side of a child's scoliotic spine.
Figure 8B:
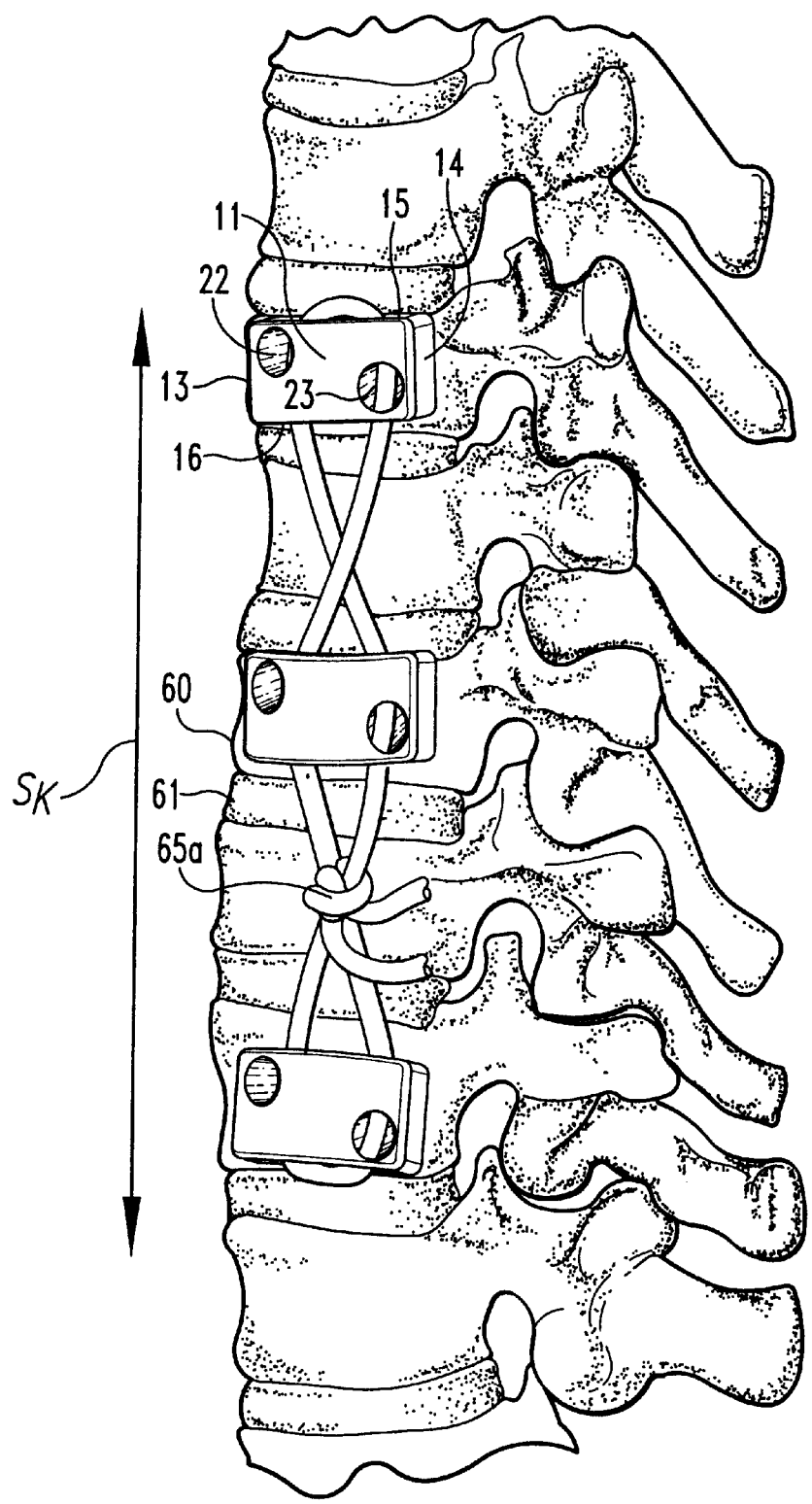
FIG. 8B is a schematic illustration of an alternative embodiment of FIG. 8A where the strand is knotted in between the blocks.
Figure 9A:
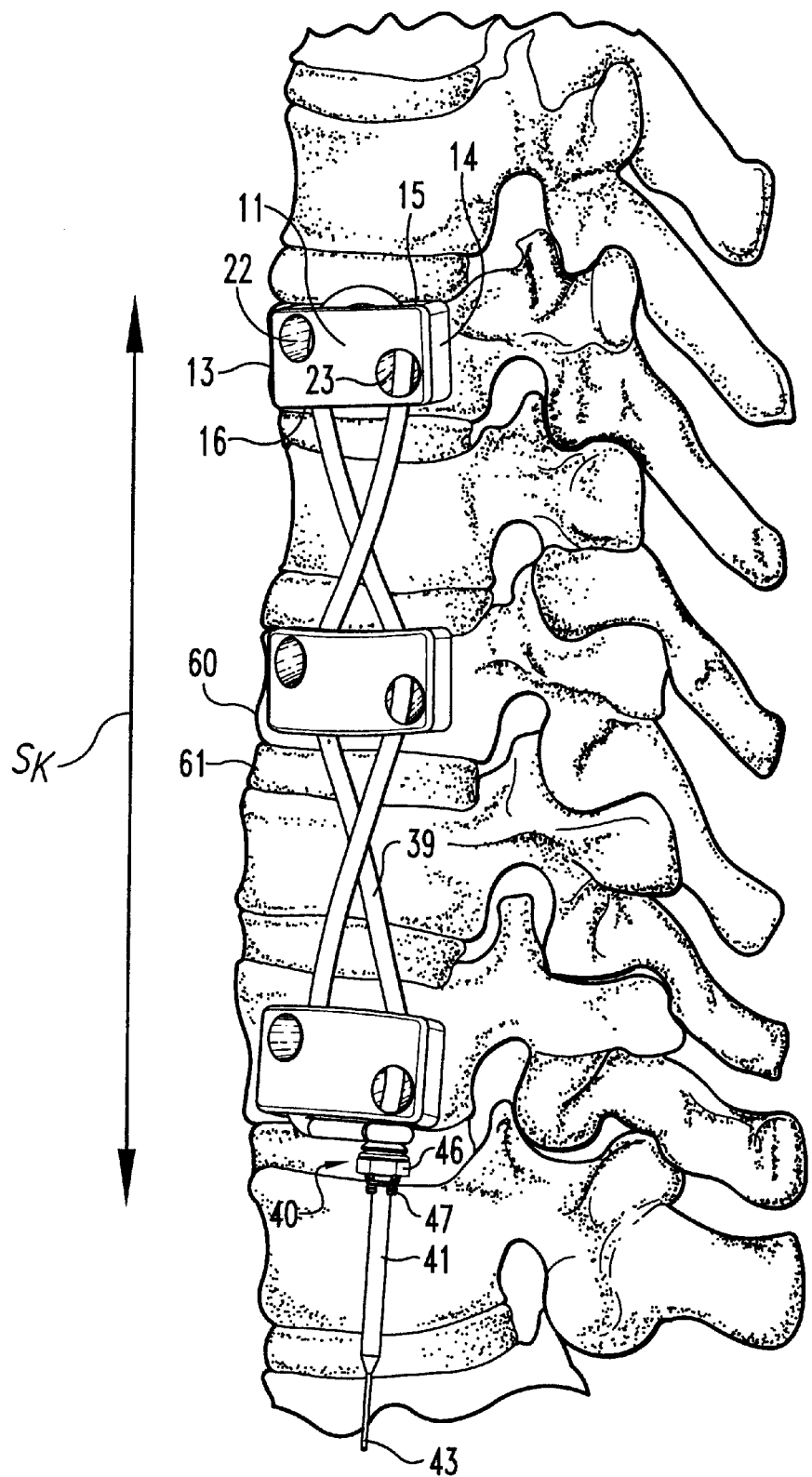
FIG. 9A is a schematic illustration of the embodiment of FIG. 5 attached to vertebral bodies on the convex side of a spine.

With reference to FIG. 3, the artificial strand 38 may be a strand with two ends tied or spliced together (see FIGS. 8A and 8B). The artificial strand 38 may be made of any suitable biocompatible material such as stainless steel or titanium or a polymer such as polyester or polyethylene. With reference to FIG. 5, another embodiment has adjustable spinal tether 40 threaded through the channels 20, 21 of blocks 10. Adjustable spinal tether 40 has a strand or cable portion 39 having a first end 41 and a second end 42. First end 41 ends in a leader 43 for ease of threading adjustable spinal tether 40 through the channels 20, 21 in blocks 10. The leader 43 may be an extrusion of first end 41 or may be otherwise affixed onto first end 41 by press fitting, adhesive, or other means known in the art. Details of various embodiments of the adjustable spinal tether construction may be found in the above mentioned patent application titled "Adjustable Spinal Tether."

Figure 6:
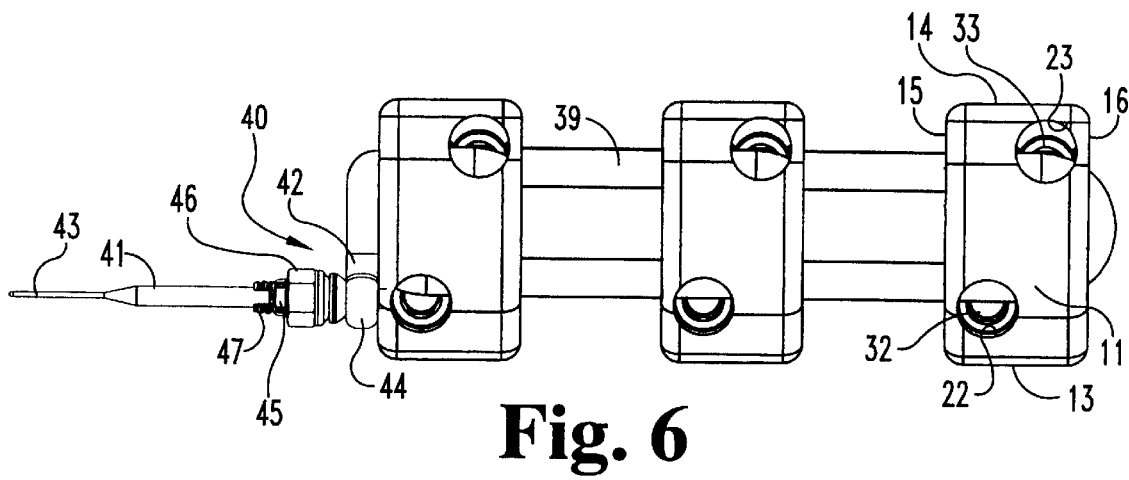
FIG. 6 is a top view of an alternative to the embodiment of FIG. 5 with the tether in a straight loop configuration.

Second end 42 may be wrapped around or otherwise attached to a grommet 44. In an alternative embodiment the adjustable spinal tether may have second end 42 looped around on itself to form an eyelet (not shown) without the need for a grommet. The leader 43 and first end 41 are threaded through grommet 44 and crimp 45 attached to the grommet 44. Crimp 45 has external threading 47 matching internal threading (not shown) on lock nut 46. Lock nut 46 is tightened down on crimp 45 to secure crimp 45 on strand or cable 39 when the appropriate length is threaded through the channels 20, 21 of blocks 10 and drawn taut. The excess length of strand 39 may then be trimmed off above crimp 45. With reference to FIGS. 3, 5 it is seen that the strand 38, 39 may be threaded through blocks 10 in a figure eight configuration. With reference to FIG. 6, in an alternative embodiment it is seen that the strand 38 may also be threaded through blocks 10 in a straight loop configuration. It should be understood that for all embodiments the strand 38 or adjustable spinal tether 40 may be threaded through the channels in the blocks 10 in either a figure eight or loop configuration or any combination of both as desired.

Figure 7:
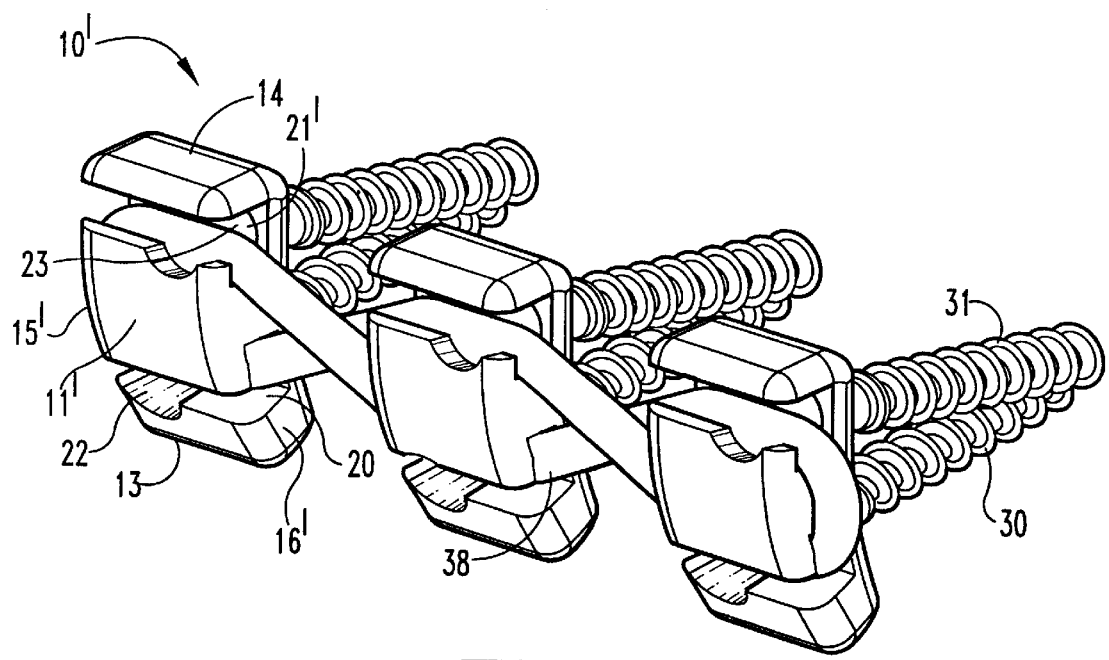
FIG. 7 is a perspective view of another embodiment in which the channels open through the top surface of the blocks.

With reference to FIG. 7, in yet another embodiment blocks 10' are shown with like elements labeled as previously. Blocks 10' have anterior channel 20' and posterior channel 21'. In this embodiment anterior channel 20' and posterior channel 21' extend between upper surface 15' and lower surface 16' as well as up through top surface 11'. Additionally, anterior channel 20' and posterior channel 21' are defined such that the portion nearer to bottom surface 12 is slightly offset from that defined in top surface 11'. The channels 20', 21' in blocks 10' permit the synthetic strand 38 to be inserted into blocks 10' through top surface 11'. Since channels 20', 21' have a slightly offset region nearer to the bottom surface 12, when synthetic strand 38 is drawn taut it is secured within the channels and will not slip out through top surface 11'.

With reference to FIG. 8A, blocks 10 are shown attached to vertebral bodies 60 with artificial strand 38 spanning intervertebral discs 61. The ends of strand 38 are shown tied together in a knot 65. It should be understood that a variety of knots may be used in place of knot 65. For example, with reference to FIG. 8B, in which like elements labeled as previously, the knot 65a may be tied in an intermediate location between two of the vertebral blocks 11 as opposed to knot 65 as seen in FIG. 8A.

Figure 9B:
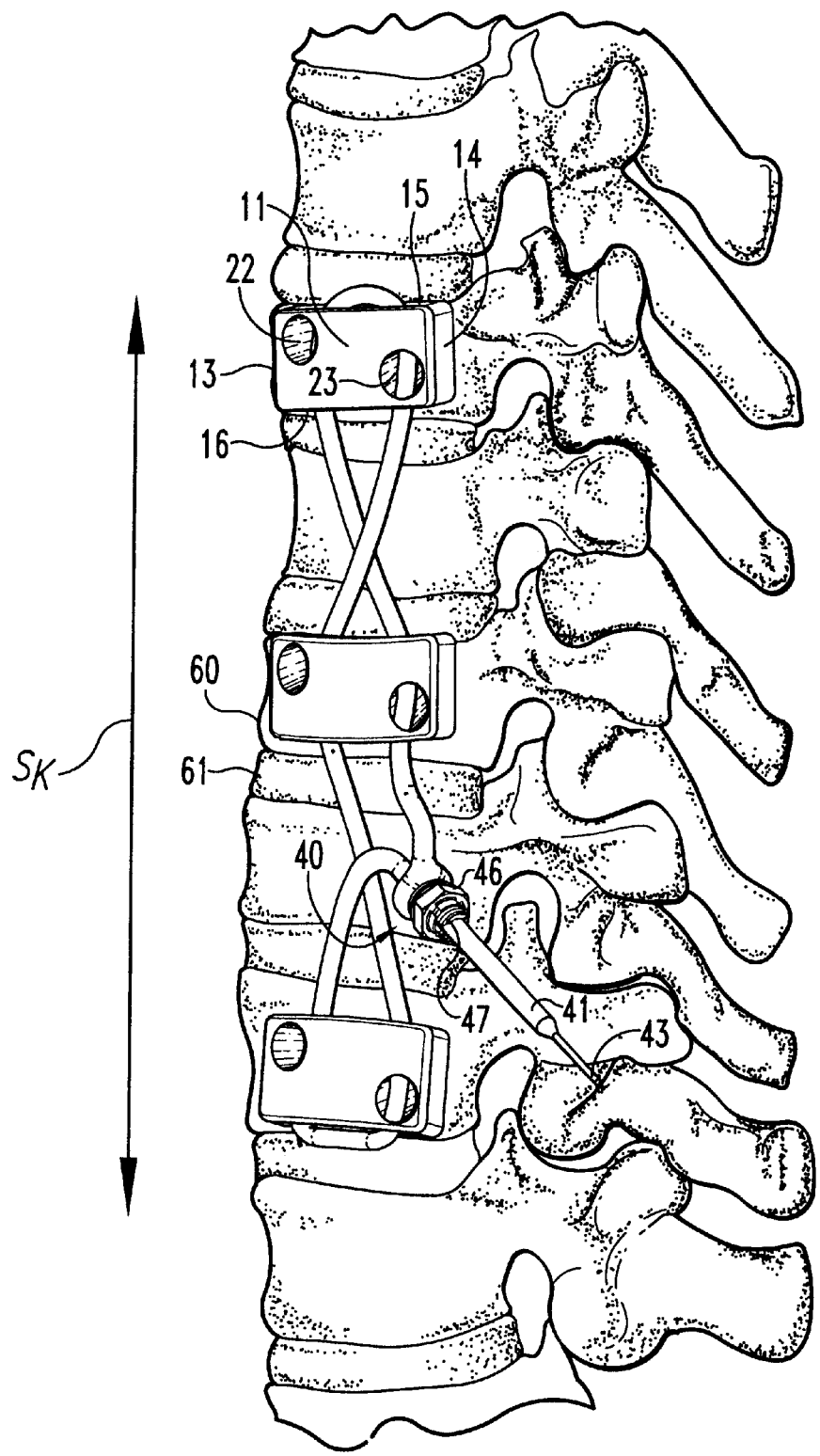
FIG. 9B is a schematic illustration of an alternative embodiment of FIG. 9A where the adjustable strand is crimped in between the blocks.

With reference to FIG. 9A, blocks 10 are again shown attached to vertebral bodies 60. In this embodiment the intervertebral discs 61 are spanned by an artificial strand 39 which is part of adjustable spinal tether 40. With reference to FIG. 9B, as in the embodiment disclosed in FIG. 8, the crimp 45 may be at an intermediate location between blocks. With reference to FIGS. 8A, 8B, 9A, and 9B, it should be noted that the arrow $S_k$ parallels the longitudinal axis of the spinal column made up of vertebral bodies and intervertebral discs.

Figure 12A:
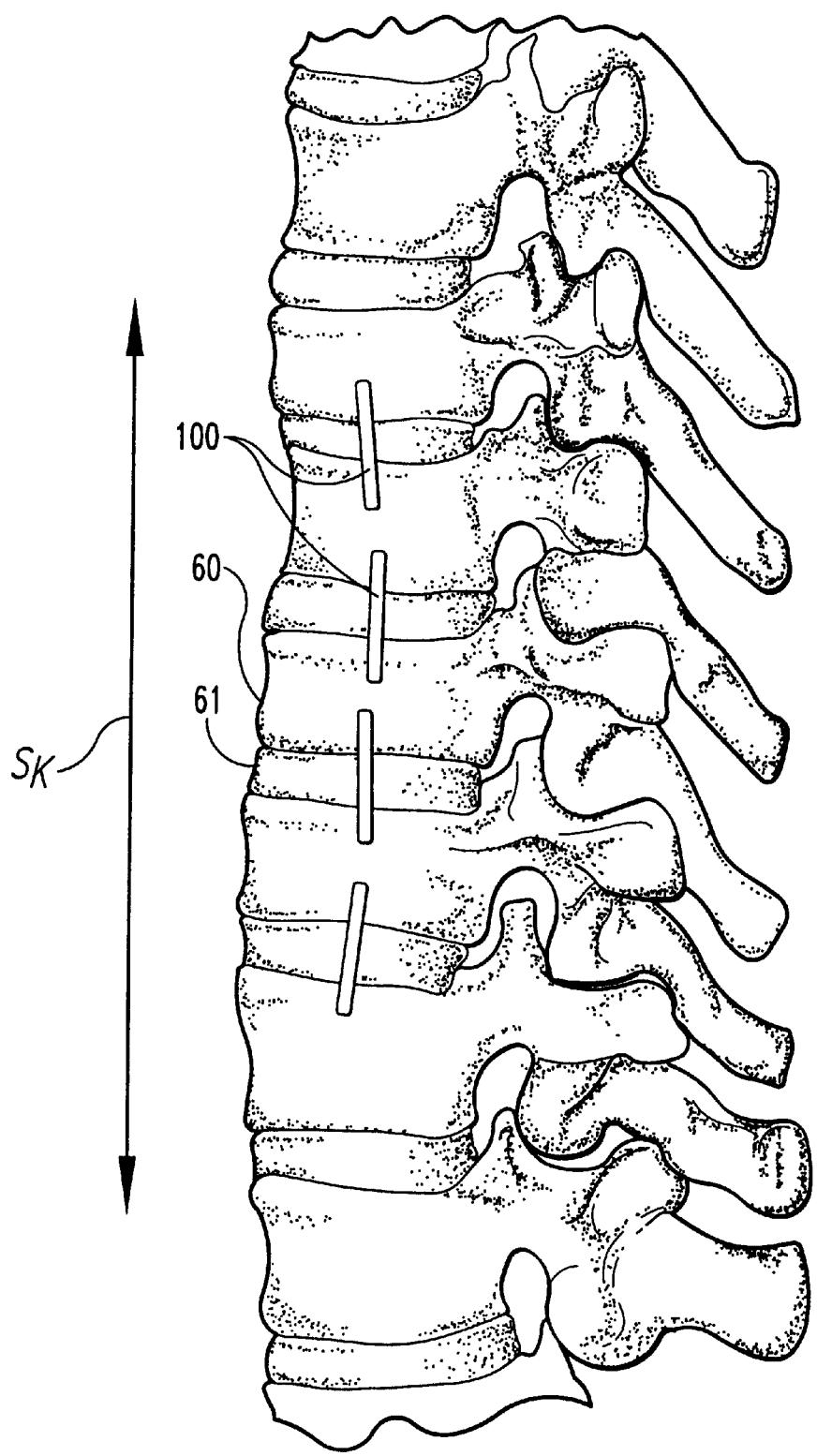
FIG. 12A is a schematic illustration of the embodiment of FIG. 1 attached to vertebral bodies on the convex side of a spine.
Figure 12B:
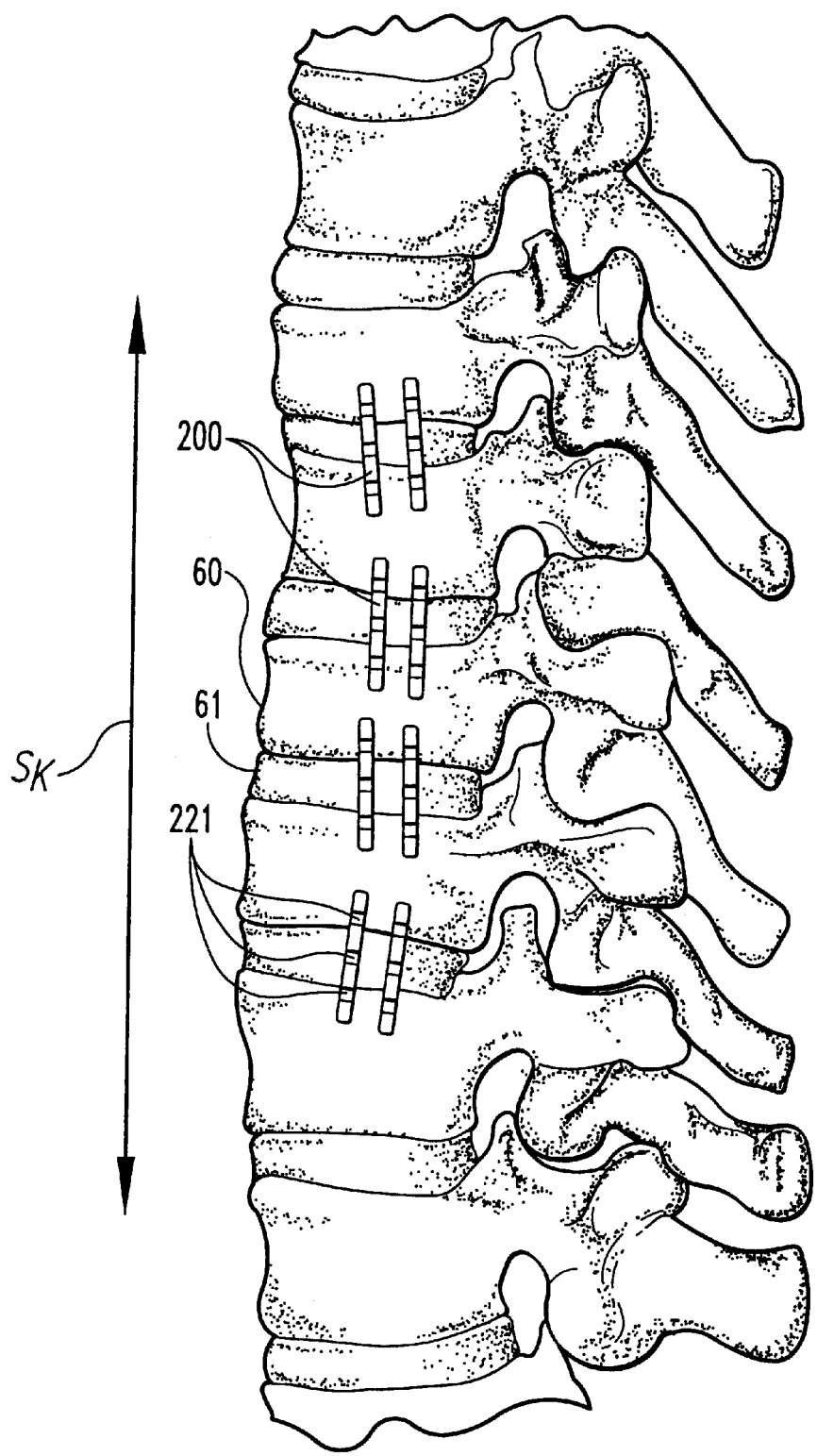
FIG. 12B is a schematic illustration of the embodiment of FIG. 13 or FIG. 14 attached to vertebral bodies on a convex side of a spine.
Figure 12C:
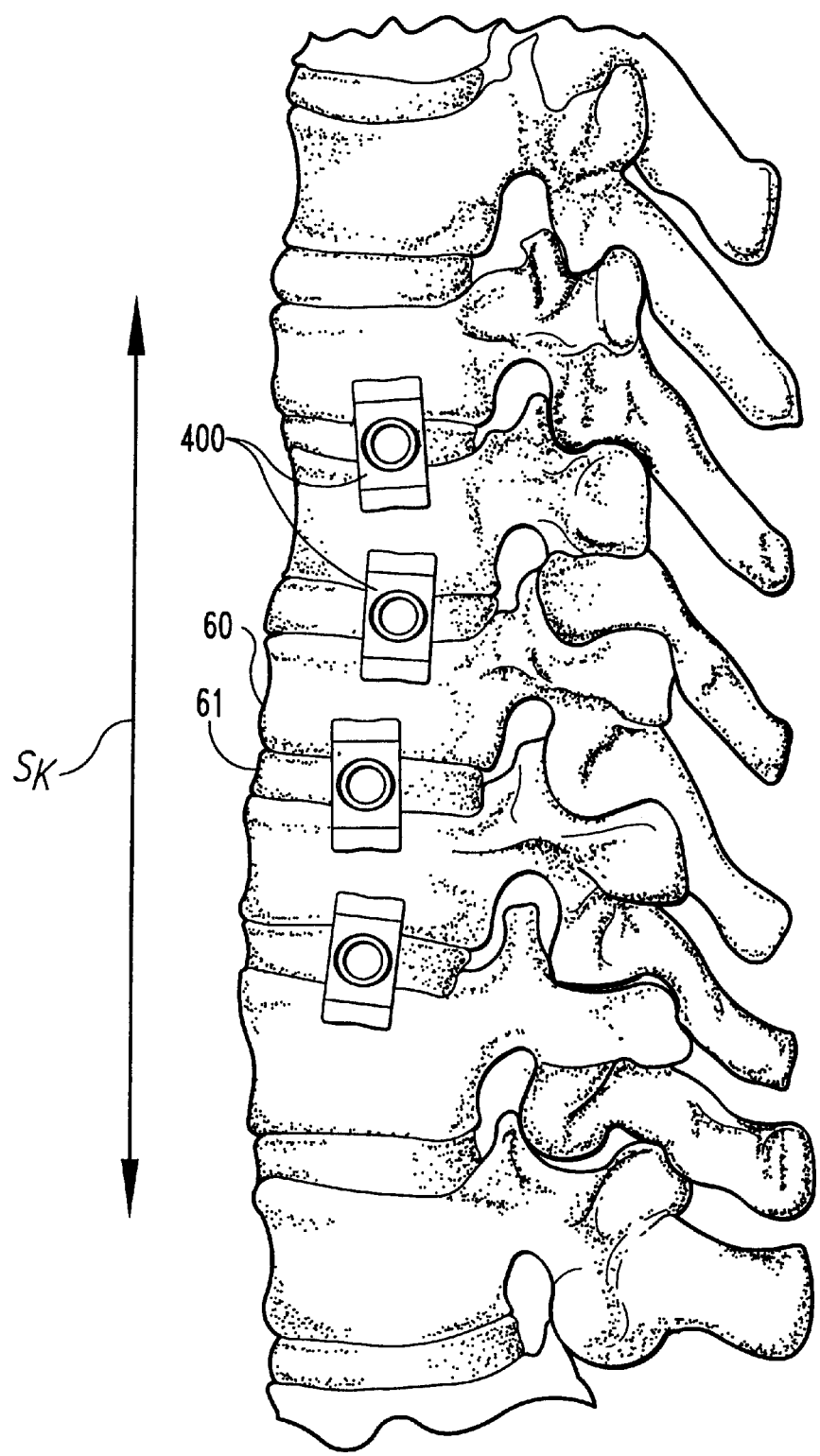
FIG. 12C is a schematic illustration of the embodiment of FIG. 15 attached to vertebral bodies on the convex side of the spine.

With reference to FIG. 12A, a plurality of spinal staples 100 with legs 102, 103 anchored in adjacent vertebral bodies 60 are shown. Crossbar 101 spans intervertebral disc 61. With reference to FIG. 12B, an embodiment is shown wherein two staples 200 are anchored in adjacent vertebral bodies 60. In this embodiment, the spinal staples 200 have notches 221 on the back of the staple for final seating of the staple into bone. This allows the surgeon to drive in each tine independently as necessary. With reference to FIG. 12C, a plurality of spinal staples 400 are anchored adjacent vertebral body 60. In this embodiment, each spinal staple 400 has four prongs. It should be understood that in each of the embodiments of FIGS. 12A–C the spinal staples may include notches on the back of the staple as desired. It should be further understood that any of the embodiments disclosed may entail the use of one, two, or even more than two spinal staples at each level.

With reference to FIGS. 13A–D, another embodiment of a spinal staple 200, such as that used in FIG. 12B is shown. Vertebral interbody staple 200 is generally u-shaped with cross bar 201 between legs 202 and 203. Staple 200 has inner surface 210 and outer surface 220. Leg 202 has a pointed tip 204 and leg 203 has a pointed tip 205 for insertion into the vertebral bodies. It should be understood that tips 204, 205 may have a variety of configurations. It should be further understood that the legs or tines in all of the embodiments in FIGS. 13–15 may have barbs on the inner surface or outer surface as desired. Similarly, it should be further understood that all of the embodiments of the staples in FIGS. 13–15 may be used in the previously described method of vertebral body tethering without fusion. The back of staple 200 has a plurality of notches 221 for final seating of the staple into the bone or vertebrae. Notches 221 aid the surgeon in driving in each tine or leg 202, 203 independently as necessary (see FIG. 12B).

To better illustrate the construction of the staple 200. the dimensions of one manufactured embodiment are hereafter listed. It should be understood, however, that these dimensions are exemplary and not intended to limit the scope of protection sought. The use of dimensions and tolerances other than those listed are contemplated as within the scope of the invention. Spinal staple 200 has a center line 215 around which it is symmetrical. An angle 225 subtended by axis 215 and a line extending from the tip 205 of leg 203 preferably defines an angle of 37 degrees. Similarly, the angle 226 from between the inner surface 210 and outer surface 220 of leg 202 is preferably 27 degrees. The width 230 of the staple 200 between tip 204 and tip 205 is preferably 9.5 mm and the greatest width 227 of staple 200 is preferably 19.5 mm. The height 232 of the notches 221 as illustrated is on the order of 0.5 mm and similarly the thickness 231 of crossbar 201 and a notch 221 is preferably approximately 2.25 mm. The height 229 of spinal staple 200 is preferably on the order of 16 mm. The distance 233 between adjacent notches 221 is approximately 1.5 mm. As previously mentioned, variations in these design parameters that would occur to a person of ordinary skill in the art are contemplated as within the scope of the invention.

With reference to FIGS. 14A–E, another embodiment of a spinal staple 300 is illustrated. Vertebral interbody staple 300 is generally u-shaped with cross bar 301 between legs 302 and 303. Staple 300 has inner surface 310 and outer surface 320. Leg 302 has a pointed tip 304 and leg 303 has a pointed tip 305 for insertion into the vertebral bodies. It should be understood that tips 304, 305 may have a variety of configurations. The back of staple 300 has a plurality of notches 321 for final seating of the staple into the bone or vertebrae. Notches 321 aid the surgeon in driving in each tine or leg 302, 303 independently as necessary.

To better illustrate the construction of the staple 300, the dimensions of one manufactured embodiment are hereafter listed. It should be understood, however, that these dimensions are exemplary and not intended to limit the scope of protection sought. The use of dimensions and tolerances other than those listed are contemplated as within the scope of the invention. Spinal staple 300 has a center line 315 around which it is symmetrical. An angle 325 subtended by axis 315 and a line extending from the tip 305 of leg 303 preferably defines an angle of 50 degrees. Similarly, the angle 326 is preferably 50 degrees. The width 330 of the staple 300 between tip 304 and tip 305 is preferably 9.5 mm and the greatest width 327 of staple 300 is preferably 17.18 mm. The height 329 of spinal staple 300 is preferably on the order of 10 mm. The distance 333 between adjacent notches 321 is approximately 2 mm. As previously mentioned, variations in these design parameters that would occur to a person of ordinary skill in the art are contemplated as within the scope of the invention.

With reference to FIGS. 15A–E, another embodiment of the shape-memory alloy staple is shown. The embodiments of the shape-memory alloy staple shown in FIGS. 13–14 are two pronged, whereas the embodiment shown in FIGS. 15A–E is a four prong staple. Shape-memory alloy staple 400 has four prongs or tines 402, 404, 406, 408 with pointed tips 403, 405, 407, and 409 respectively. The legs 402, 404, 406, 408 are interconnected by a cross plate 401. The staple 400 is symmetrical about the imaginary axis 415 which bisects the width of the staple 400. Crossbar or cross plate 401 has a bore 450 defined therein extending between outer surface 420 and inner surface 410. The bore 450 is defined by a tapered insertion surface 460 adjoining a surface 461 generally parallel to the axis 415. Bore 450 is intended to receive a fastener such as a screw or a bolt. This fastener may be attached to other fasteners received in the bores of other staples by an artificial strand or adjustable tether such as those previously described in the application entitled "Adjustable Spinal Tether."

To better illustrate the construction of the staple 400, the dimensions of one manufactured embodiment are hereafter listed. It should be understood, however, that these dimensions are exemplary and not intended to limit the scope of protection sought. The use of dimensions and tolerances other than those listed are contemplated as within the scope of the invention.

The greatest width 427 of staple 400 is on the order of 19.5 mm. The lesser width 430 separating pointed tips 403 and 407 or 405 and 409 respectively is on the order of 9.5 mm. Preferably bore 450 has a circular cross section defined by surface 461 having a diameter on the order of 6.5 mm. The thickness 431 of crossbar or cross plate 401 is on the order of 2.25 mm. The width 428 of crossbar or cross plate 401 is on the order of 10 mm. The height 429$b$ defined between the pointed tips of the legs of the staple 400 and the arch formed between adjacent legs 402 and 404 or 406 and 408 respectively is approximately 12 mm. The total height 429$a$ from the pointed tips to the top most portion of the back of the staple as defined by cross plate 401 is approximately 16 mm. The height 462 of tapered insertion surface 460 along axis 415 parallel to the axis 415 is approximately 1 mm. The width 470 of the arch formed between adjacent legs 406 and 408 or 402 and 404 respectively is approximately 6 mm. The angles 426 subtended by each tip 403, 405, 407, and 409 between inner surface 410 and outer surface 420 is approximately 27 degrees. Similarly, the angle 425 subtended between axis 415 and a line tangential to the outer surface 420 at any of the tips is approximately 37 degrees. As previously mentioned, variations in these design parameters that would occur to a person of ordinary skill in the art are contemplated as within the scope of the invention.

Figure 14D:
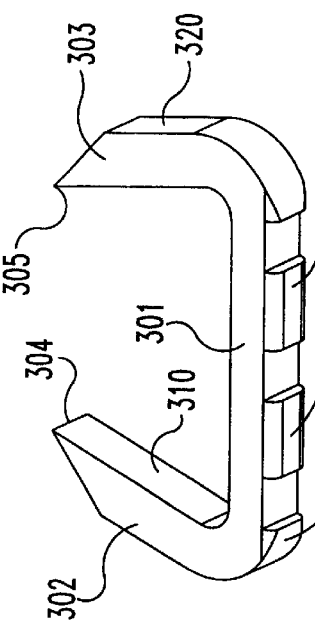
FIG. 14D is a perspective view of the embodiment of the spinal staple of FIG. 14A.
Figure 14E:
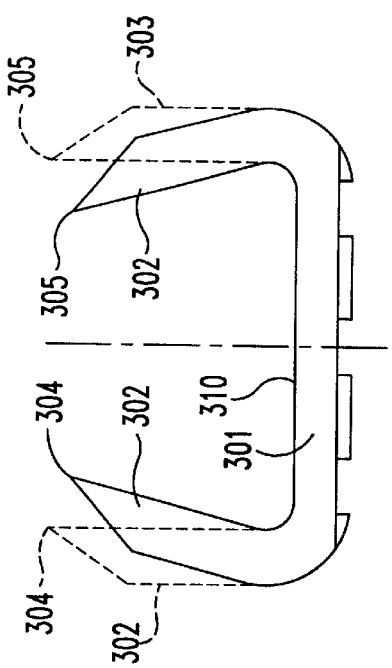
FIG. 14E is a side view of the embodiment of the spinal staple of FIG. 14A showing the tines in the insertion position in phantom.
Figure 14C:
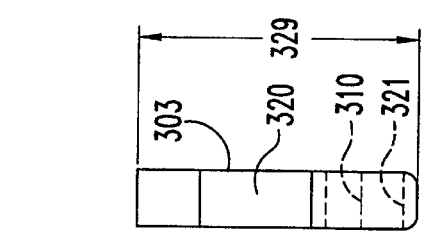
FIG. 14C is a side view of the embodiment of FIG. 14A.
Figure 14B:
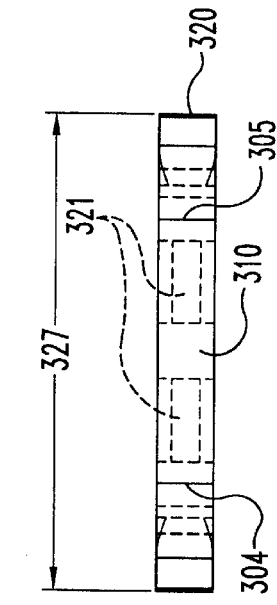
FIG. 14B is a top view of the embodiment of FIG. 14A.
Figure 14A:
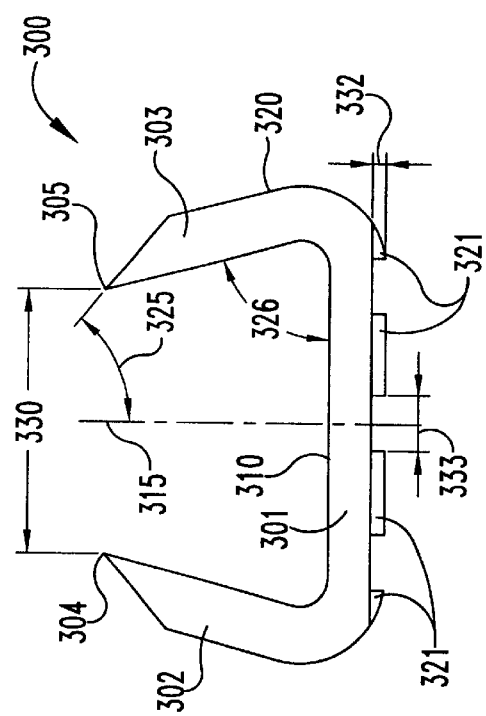
FIG. 14A is a side view of another embodiment of a spinal staple.

With reference to FIGS. 13D, 14E and 15E, the deformed martensitic insertion shape of the legs of the staples is shown in phantom. It should be understood that this deformed state may arise from the formation of martensite because of temperature conditions or the formation of stress induced martensite from the application of a force. After the various embodiments of the staples are inserted in their open position, either the stress is released or the staple is heated to reform the staple to its closed memorized shape.

With reference to FIGS. 16A–I, another embodiment of an anterior block for spine tethering is shown. Each block 510 has a top surface 511, a bottom surface 512, intermediate surfaces 551, 552, and first and second sets of opposing side surfaces. The block 510 is oriented so that the first set of side surfaces 513$a$, 513$b$, and 514$a$, 514$b$ are located on an anterior and a posterior part respectively of the spine (similar to side surfaces 13 and 14 in FIGS. 8 and 9). The first set of side surfaces includes an upper anterior side surface 513$a$ and a lower anterior side surface 513$b$ and an upper posterior side surface 514$a$ and lower posterior side surface 514$b$. The block 510 has a generally curved shape in a transverse direction from the lower anterior surface 513$b$ to the lower posterior surface 514$b$ corresponding to the antero-lateral anatomy of vertebral bodies. The bottom surface 512 is preferably (but not necessarily) configured to contact the vertebral body.

Each block 510 has a second set of side surfaces 515, 516 which are oriented to face substantially upward and downward along the longitudinal axis of the spine, similar to side surfaces 15, 16 in FIGS. 8 and 9. The upper surface 515 and lower surface 516 of each block 510 define at least one opening or channel for receiving a synthetic strand or adjustable spinal tether. In an embodiment with only one channel, the channel must either have a post or divider somewhere along its length around which the strand or adjustable spinal tether is wrapped or, alternatively, the strand or adjustable spinal tether may be threaded through the channel and around either the top surface 511 or bottom surface 512 of each block 510. In one preferred embodiment (see FIGS. 16A–I), each block 510 has two substantially parallel channels, an anterior channel 520 and a posterior channel 521. Anterior channel 520 and posterior channel 521 extend in a direction along a line connecting upper surface 515 and lower surface 516. It is contemplated as within the scope of the invention that anterior channel 520 and posterior channel 521 may extend in different directions and/or be curved in between upper surface 515 and lower surface 516. It is further contemplated as within the scope of the invention that anterior channel 520 and posterior channel 521 may be at an angle with respect to either or both of upper surface 515 and lower surface 516. Moreover, channels 520 and 521 may both be closer to anterior surface 513 than posterior surface 514 or vice versa. Selection of various channel orientations permits configurations for the synthetic strand or adjustable spinal tether or than the figure eight or straight loop configuration shown in FIGS. 5 and 6 with reference to a previously described embodiment of the block. Also, it should be understood that the channels such as 520 and 521 may instead connect the first set of opposing upper side surfaces 513a and 514a or may connect some combination of the first and second sets of opposing side surfaces.

Additionally, each block 510 further defines at least one bore extending between top surface 511 and bottom surface 512. Each block 510 may have one or more bores for receiving a fastener or connect each block to a vertebral body. In one preferred embodiment, block 510 has two bores, an anterior bore 522 and a posterior bore 523. It should be understood that each block 510 may have only one bore or more than two depending on the number of fasteners a surgeon wishes to use to attach each block to a vertebral body. Each bore 522, 523 extends between the top surface 511 and bottom surface 512 of block 510. Bores 522, 523 are defined in block 510 with dimensions such that each bore may receive one of the fasteners used to attach the block 510 to the vertebral body.

It should be understood that the bores of this embodiment of the anterior block may include features similar to those described in the previous embodiment and shown in FIGS. 10 and 11. In other words, the bores may have tapered surfaces for facilitating insertion of fasteners, may be shaped for a ball and socket interconnection, may have matching threading on the head of a fastener to prevent screw back out and the bores may be arranged in a variety of angles with respect to each other. These and other features were previously described with reference to the embodiment shown in FIGS. 10 and 11.

Figure 16D:
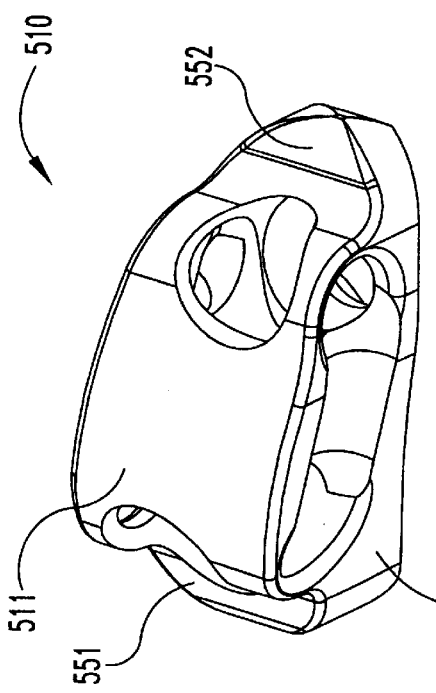
FIG. 16D is a perspective view of the embodiment of the block of FIG. 16A.
Figure 16C:
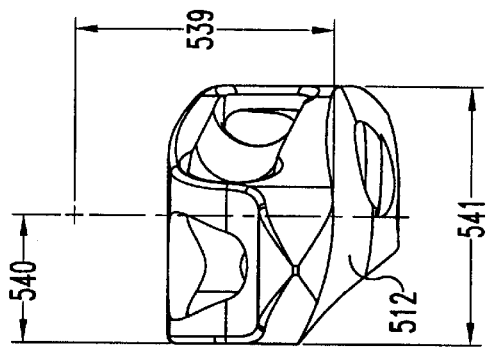
FIG. 16C is another side view of the embodiment of the block in FIG. 16A.
Figure 16B:
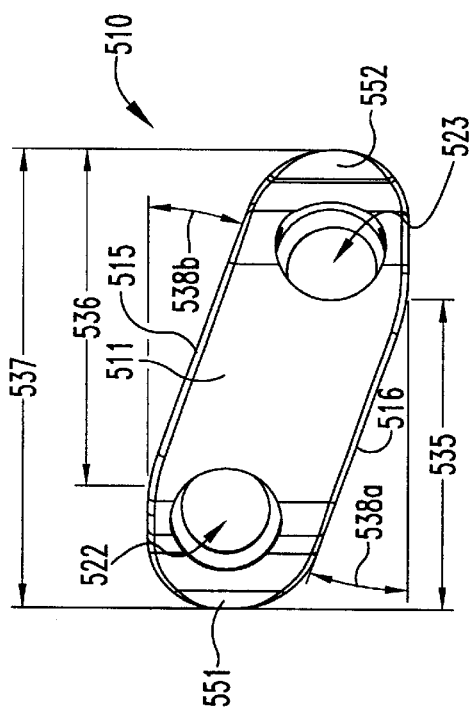
FIG. 16B is a top view of the embodiment of the block of FIG. 16A.
Figure 16A:
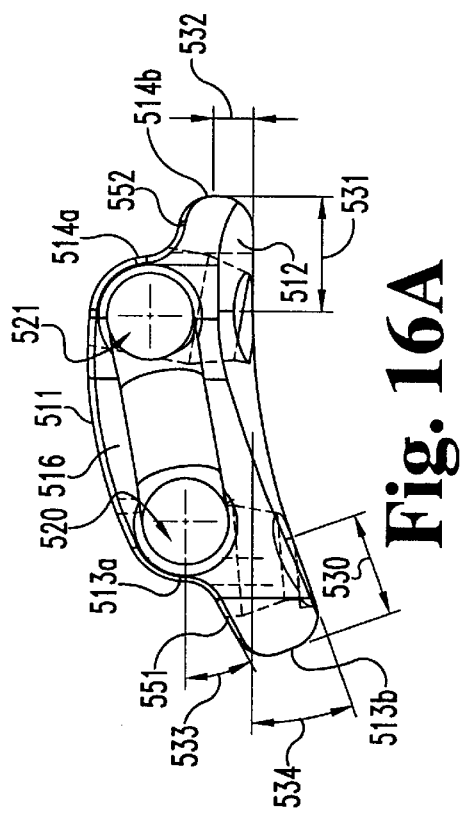
FIG. 16A is a side view of another embodiment of a block.
Figure 16I:
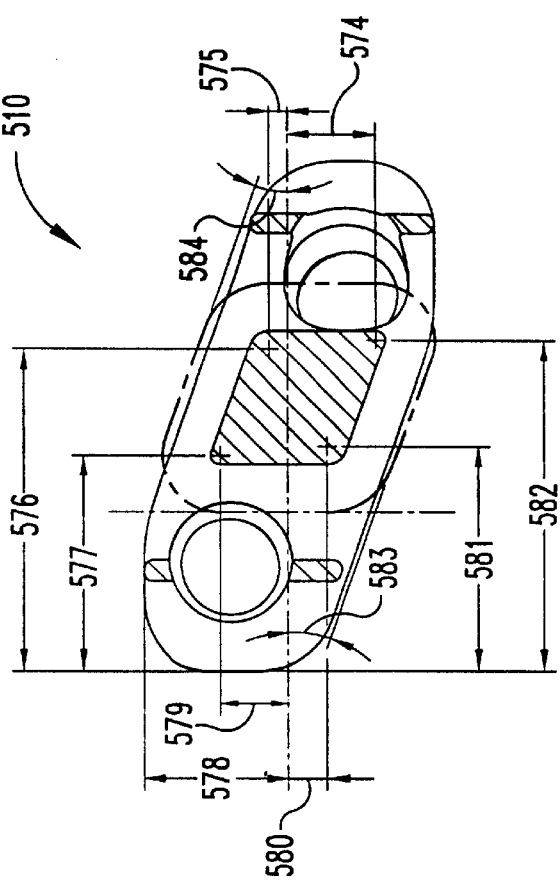
FIG. 16I is a cross-sectional view of FIG. 16H along the lines 161.
Figure 16H:
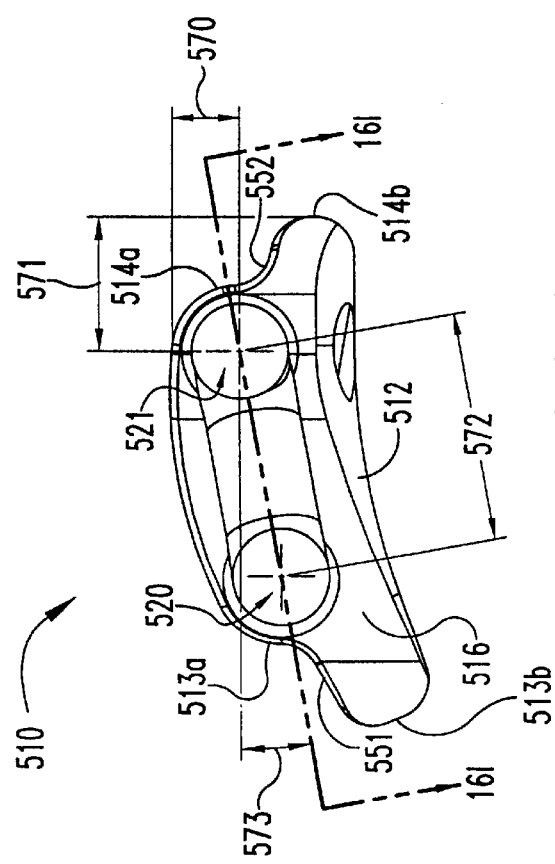
FIG. 16H is another side view of the embodiment of FIG. 16A illustrating further detail.

To better illustrate the construction of the block 510, the dimensions of one manufactured embodiment are hereafter listed. It should be understood, however, that these dimensions are exemplary and not intended to limit the scope of protection sought. The use of dimensions and tolerances other than those listed are contemplated as within the scope of the invention. With reference to FIG. 16A, length 530 is 6 mm, length 531 is 6.7 mm, length 532 is 2.33 mm, angle 533 is 30 degrees, and angle 534 is 20 degrees. With reference to FIG. 16B, length 535 is 17.82 mm, length 536 is 19.16 mm, length 537 is 26.39 mm, and angles 538a and 538b are both preferably 20 degrees. With reference to FIG. 16C, length 539 is 15 mm, length 540 is 7.5 mm, and length 541 is 15 mm. With reference to FIG. 16E, length 542 is 10.5 mm, 543 is 4.5 mm. With reference to FIG. 16F, length 544 is 10.6 mm, length 545, which defines the diameter of bore 523 at one point is 6.4 mm, length 546 is 20, length 547, which defines the diameter of the bore at one point, is 6 mm, length 548, which defines the minimum diameter of the bore is 5.05 mm, and angle 549 is five degrees. With reference to FIG. 16G, length 560 is 8.4 mm, and length 563 is 7 mm, angle 564 is 15 degrees and angle 565 is 10 degrees. With reference to FIG. 16H, length 570 is 3.1 mm, length 571 is 7 mm, length 572 is 12 mm, and angle 573 is 10 degrees. With reference to FIG. 16I, length 574 is 4.53 mm, length 575 is 1 mm, length 576 is 16.85 mm, length 577 is 11.35 mm, length 578 is 7.5 mm, length 579 is 3.53 mm, length 580 is 2 mm, length 581 is 11.85 mm, length 582 is 17.35 mm, and angles 583 and 584 are both 20 degrees. As previously mentioned, variations in these design parameters that would occur to a person of ordinary skill in the art are contemplated as within the scope of the invention.

It should be understood that the just described embodiment of a block may be used in various manners similar or identical to those shown in FIGS. 3–9 with an artificial strand or adjustable tether. The advantages of this embodiment include the reduction in the amount of volume and the amount of metal. By essentially removing portions of what was a previously rectangular cross section, this embodiment of the block has a lower profile and is less bulky.

It was previously mentioned that various problems exist in the prior art. Fusionless tethering addresses several of these problems. For example, curve stabilization with thoracoscopic stapling would subject patients with juvenile scoliosis to fewer and less destructive procedures. Also, while anterior and/or posterior spinal fusion in the skeletally immature patient often results in loss of vertebral body height and girth, thoracoscopic stapling would allow continued growth of the remaining vertebral body. The removal of the staples or other fusionless tethers after correction of the deformity permits further growth, thus minimizing the loss of vertebral body height and girth. Another problem mentioned is that some children, while not currently candidates for a definitive fusion procedure, are likely to need such a procedure in the future. Fusionless tethering of the convex side generally, and vertebral interbody stapling in particular, offers an alternative method of curve stabilization for these children. This method allows such children to continue growth while their curve is restrained from progression.

While the invention has been illustrated and described in detail in the drawings and foregoing description, the same is to be considered illustrative and not restrictive in character, it being understood that only the preferred embodiments have been shown and described and that all changes and modifications that come within the spirit of the invention are desired to be protected.

What is claimed:

1. A method of treating a spinal curvature having a convex side and a concave side, comprising:
    flexibly constraining curve progression along the convex side of the spinal curvature without application of a substantial external corrective force.

2. A method of treating a spinal curvature having a convex side and a concave side, comprising:

flexibly constraining curve progression along the convex side of the spinal curvature by securing a flexible tether directly to the at least two vertebral bodies.

3. A method of treating a spinal curvature having a convex side and a concave side, comprising:

flexibly constraining curve progression along the convex side of the spinal curvature by attaching a flexible tether to the at least two vertebral bodies, the flexible tether comprises at least one staple and wherein the attaching comprises driving the at least one staple into adjacent ones of the at least two vertebral bodies along the convex side of the spinal curvature to span the disc space separating the adjacent ones of the vertebral bodies.

4. The method of claim 3 wherein the at least one staple is at least partially formed of a shape-memory material.

5. A method of treating a spinal curvature having a convex side and a concave side, comprising:

flexibly constraining curve progression along the convex side of the spinal curvature by minimizing growth along the convex side of the spinal curvature while permitting growth along the concave side of the spinal curvature.

6. The method of claim 5 wherein the flexibly constraining comprises attaching a flexible tether to the at least two vertebral bodies bone anchor comprises a staple.

7. The method of claim 6 wherein the attaching comprises engaging a bone anchor to a respective one of the at least two vertebral bodies and securing the flexible tether to each of the bone anchors.

8. The method of claim 7 wherein the bone anchor comprises a screw.

9. The method of claim 7 wherein the bone anchor comprises a staple.

10. The method of claim 6 wherein the flexible tether comprises a strand.

11. The method of claim 6 wherein the flexible tether is formed of a polymeric material.

12. The method of claim 6 wherein the flexible tether is formed of a synthetic material.

13. The method of claim 6 wherein the flexible tether is at least partially formed of a shape-memory material.

14. The method of claim 13 wherein the shape-memory material exhibits superelastic characteristics at about body temperature.

15. The method of claim 5 wherein treatment of the spinal curvature occurs without fusion.

16. A method of treating a spinal curvature having a convex side and a concave side, comprising:

flexibly constraining growth along the convex side of the spinal curvature without application of a substantial external corrective force.

17. A method of treating a spinal curvature having a convex side and a concave side, comprising:

flexibly constraining growth along the convex side of the spinal curvature by attaching a flexible tether to the at least two vertebral bodies, the flexible tether comprises at least one staple at least partially formed of a shape-memory material, and wherein the attaching comprises inserting the at least one staple into adjacent ones of the at least two vertebral bodies along the convex side of the spinal curvature to span the disc space separating the adjacent ones of the vertebral bodies.

18. A method of treating a spinal curvature having a convex side and a concave side, comprising:

flexibly constraining growth along the convex side of the spinal curvature by minimizing growth along the convex side of the spinal curvature while permitting growth along the concave side of the spinal curvature.

19. The method of claim 18 wherein the flexibly constraining comprises attaching a flexible tether to the at least two vertebral bodies.

20. The method of claim 19 wherein the attaching comprises engaging a bone anchor to a respective one of the at least two vertebral bodies and securing the flexible tether to each of the bone anchors.

21. The method of claim 19 wherein the flexible tether is at least partially formed of a shape-memory material.

22. The method of claim 21 wherein the shape-memory material exhibits superelastic characteristics at about body temperature.

23. A method of treating a spinal curvature having a convex side and a concave side, comprising:

providing a tether at least partially formed of a shape-memory material;

attaching the tether to at least two vertebral bodies; and constraining curve progression along the convex side of the spinal curvature without application of a substantial external corrective force.

24. The method of claim 23 wherein the tether comprises at least one staple.

25. The method of claim 23 wherein the tether flexibly constrains curve progression along the convex side of the spinal curvature.

26. The method of claim 23 further comprising constraining growth along the convex side of the spinal curvature.

27. The method of claim 23 wherein the attaching comprises engaging a bone anchor to a respective one of the at least two vertebral bodies and securing the tether to each of the bone anchors.

28. A method of treating a spinal curvature having a convex side and a concave side, comprising:

providing a tether at least partially formed of a shape-memory material;

attaching the tether to at least two vertebral bodies; and constraining curve progression along the convex side of the spinal curvature; and wherein the tether comprises at least one staple and the attaching comprises inserting the staple into the at least two vertebral bodies along the convex side of the spinal curvature.

29. The method of claim 28 wherein the attaching comprises inserting the staple into adjacent ones of the at least two vertebral bodies along the convex side of the spinal curvature to span the disc space separating the adjacent ones of the vertebral bodies.

30. A method of treating a spinal curvature having a convex side and a concave side, comprising:

providing a tether at least partially formed of a shape-memory material;

attaching the tether to at least two vertebral bodies; and constraining curve progression along the convex side of the spinal curvature;

wherein the tether comprises at least one staple, the staple including a first prong, a second prong, and a connector portion interconnecting the first and second prongs, the shape-memory material being transitionable between a deformed state and a memorized state, the first and second prongs being disposed closer to one another in the memorized state than in the deformed state; and wherein the attaching comprises inserting the staple into the at least two vertebral bodies when in the deformed state and transitioning the shape-memory material toward the memorized state.

31. The method of claim 30 wherein the first and second prongs are substantially parallel when in the deformed state and are angled toward one another when transitioned toward the memorized state.

32. The method of claim 30 wherein each of the first and second prongs includes a distal portion, the distal portions being disposed closer to one another in the memorized state than in the deformed state.

33. The method of claim 30 wherein the transitioning occurs without a corresponding change in temperature.

34. A method of treating a spinal curvature having a convex side and a concave side, comprising:

providing a tether at least partially formed of a shape-memory material;

attaching the tether to at least two vertebral bodies; and constraining curve progression along the convex side of the spinal curvature;

wherein the tether comprises at least one staple, the staple including a first prong, a second prong, and a connector portion interconnecting the first and second prongs, the connector portion being at least partially formed of the shape-memory material, the shape-memory material exhibiting superelastic characteristics at about body temperature to flexibly constrain curve progression along the convex side of the spinal curvature.

35. A method of treating a spinal curvature having a convex side and a concave side, comprising:

providing a tether at least partially formed of a shape-memory material;

attaching the tether to at least two vertebral bodies; and constraining curve progression along the convex side of the spinal curvature;

wherein the shape-memory material exhibits superelastic characteristics at about body temperature to flexibly constrain curve progression along the convex side of the spinal curvature.

* * * * *